United States Patent
Takashima et al.

(10) Patent No.: US 6,413,752 B1
(45) Date of Patent: Jul. 2, 2002

(54) PROTEIN CAPABLE OF CATALYZING TRANSAMINATION STEREOSELECTIVELY, GENE ENCODING SAID PROTEIN AND USE THEREOF

(75) Inventors: Yoshiki Takashima, Nishinomiya; Satoshi Mitsuda, Takarazuka; Marco Wieser, Mino, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/527,522

(22) Filed: Mar. 16, 2000

(30) Foreign Application Priority Data

Mar. 19, 1999 (JP) .......................... 11-075511
Mar. 30, 1999 (JP) .......................... 11-088634

(51) Int. Cl.[7] ................................ C12N 9/10
(52) U.S. Cl. ................................... 435/193
(58) Field of Search .......................... 435/193

(56) References Cited

U.S. PATENT DOCUMENTS 5,965,432 A 10/1999 Kobayashi et al. ......... 435/280

FOREIGN PATENT DOCUMENTS

| EP | 0 404146 A | 12/1990 |
|---|---|---|
| EP | 0857790 A1 | 8/1998 |
| EP | 0987332 A1 | 3/2000 |
| JP | 61-187786 A | 8/1986 |
| WO | WO 98 48030 A | 10/1998 |
| WO | WO 99 46398 A | 9/1999 |
| WO | WO 00 26351 A | 5/2000 |

OTHER PUBLICATIONS

Database WPI Section Ch, Week 198013, Derwent Publications Ltd., London, GB: An 1980–22950C XP002142724 & JP 55022630A (Mitsui Toatsu Chem. Inc.), Abstract.

Database WPI Section Ch, Week 198604, Derwent Publications Ltd., London, GB: An 1986–025607 XP002142725 & JP 60 248647A (Yamakawa Yakuhin KK), Dec. 9, 1985), Abstract.

Shin Jong–Shik et al., "asymmetric synthesis of chiral amines with omega–transaminase." Biotechnology and Bioengineering., vol. 65, No. 2, Oct. 20, 1999, pp. 206–211 XPOO214278 ISSN: 0006–3592 728.

*Primary Examiner*—Elizabeth Slobodyansky
(74) *Attorney, Agent, or Firm*—Sughrue Mion, PLLC

(57) ABSTRACT

A novel protein from *Mycobacterium aurum* SC-D423 capable of converting acetophenone to an optically active 1-phenylethylamine in the presence of a racemic mixture of sec-butylamine is provided.

13 Claims, No Drawings

PROTEIN CAPABLE OF CATALYZING TRANSAMINATION STEREOSELECTIVELY, GENE ENCODING SAID PROTEIN AND USE THEREOF

BACKGROUND OF THE INVENTION

1. Field of the Invention

The present invention relates to a protein capable of catalyzing transamination stereoselectively, a gene encoding said protein and uses thereof.

2. Description of the Related Art

An optically active amino compound represented by Formula (3):

$$X^1-C^*H(NH_2)-(CH_2)_m-R^1 \quad (3)$$

(wherein $X^1$ is an optionally substituted $C_1-C_9$ alkyl group, an optionally substituted $C_6-C_{14}$ aryl group, an optionally substituted $C_7-C_{17}$ arylalkyl group, an optionally substituted $C_4-C_{12}$ heteroaryl group, an optionally substituted $C_5-C_{15}$ heteroarylalkyl group, an amino group, an aminocarbonyl group, a hydroxyl group, a thiol group, a guanidyl group, a cyano group, a halogen atom or a hydrogen atom, $R^1$ is a $C_1-C_6$ alkyl group, a carboxyl group, $C_2-C_6$ alkyloxycarbonyl group or a hydrogen atom, m is an integer of 0 to 6, and * is an asymmetric carbon atom, is a compound which is useful as an intermediate for synthesizing a compound utilizable in various applications.

For example, an optically active form of an amino group-containing compound represented by Formula (10):

$$X^5-(CH_2)_r-CH(NH_2)-R^9 \quad (10)$$

(wherein $X^5$ is an optionally substituted phenyl or an optionally substituted naphthyl group, $R^9$ is a $C_1-C_6$ alkyl group, and r is an integer of 0 to 4), is a compound which is useful as an intermediate for synthesizing a pharmaceutical such as a diabetes-treating agent, an anti-obesity agent, a bronchodilator and the like, as well as a pesticide such as a fungicide, a herbicide and the like, while an optically active amino compound represented by Formula (8):

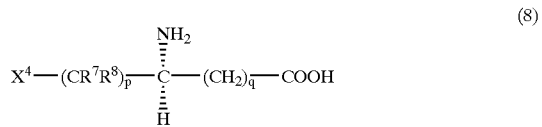

(wherein $X^4$ is an optionally substituted $C_6-C_{14}$ aryl group, an optionally substituted $C_4-C_{12}$ heteroaryl group, an optionally substituted $C_1-C_3$ alkyl group, an amino group, an aminocarbonyl group, a hydroxyl group, a thiol group, a guanidyl group or a hydrogen atom, $R^7$ and $R^8$ may be the same or different and each is a hydrogen atom or a $C_1-C_3$ alkyl group, p is an integer of 0 to 3 and q is an integer of 0 to 2) is a compound which is useful as an intermediate for synthesizing a pharmaceutical such as a growth-disorder treating agent, anti-coagulant, carcinostatic and the like.

A known biocatalyst used in a production of an optically active amino compound described above is, for example, a transaminase derived from a microorganism belonging to the genus Arthrobacter which has an ability to produce an optically active amine compound from a certain ketone compound as a starting material (WO97/15682, WO98/48030). A D-amino acid transaminase derived from a microorganism belonging to the genus of Bacillus which has an ability to produce an optically active D-amino acid from a certain keto acid compound as a starting material (JP-B-5-5472) is also known.

SUMMARY OF THE INVENTION

The objective of the present invention is to provide a novel protein which has an excellent ability to produce an optically active amino compound efficiently, a gene encoding said protein and uses thereof.

Considering such circumstances, the present inventors have intensively investigated biocatalysts for producing an optically active amino compound. As a result, they have found a novel protein capable of catalyzing transamination stereoselectively and a gene encoding said protein and uses thereof, and have accomplished the present invention.

That is, the present invention provides:

1. A protein having any one of the following amino acid sequences (hereinafter referred to as "the protein of the present invention"):
   (a) an amino acid sequence represented by Sequence ID No. 1;
   (b) an amino acid sequence comprising an amino acid substitution occurring at a part corresponding to a part of an amino acid sequence represented by Sequence ID No. 1;
   (c) an amino acid sequence of a protein capable of converting acetophenone to an optically active 1-phenylethylamine in the presence of a racemic mixture of sec-butylamine, said amino acid sequence showing an amino acid identity with the amino acid sequence represented by Sequence ID No. 1 of 60% or higher;
   (d) an amino acid sequence of a protein capable of converting acetophenone to an optically active 1-phenylethylamine in the presence of a racemic mixture of sec-butylamine and having a molecular weight of about 37 kDa as a monomer, said amino acid sequence showing an amino acid identity with the amino acid sequence represented by Sequence ID No. 1 of 80% or higher; and,
   (e) an amino acid sequence of a protein capable of converting acetophenone to an optically active 1-phenylethylamine in the presence of a racemic mixture of sec-butylamine and derived from a microorganism belonging to the genus Mycobacterium, said amino acid sequence showing an amino acid identity with the amino acid sequence represented by Sequence ID No. 1 of 60% or higher.
2. A protein having an amino acid sequence represented by Sequence ID No. 1.
3. A protein having an amino acid sequence comprising an amino acid substitution from threonine to alanine occurring at a position corresponding to amino acid's position No.2 of an amino acid sequence represented by Sequence ID No. 1;
4. A protein having a molecular weight of about 37 kDa as a monomer which is obtainable from *Mycobacterium aurum* SC-S423 and which is capable of converting acetophenone to an optically active 1-phenylethylamine in the presence of a racemic mixture of sec-butylamine.
5. A gene encoding a protein having any one of the following amino acid sequences (hereinafter referred to as "the gene of the present invention"):
   (a) an amino acid sequence represented by Sequence ID No. 1;
   (b) an amino acid sequence comprising an amino acid substitution occurring at a part corresponding to a part of an amino acid sequence represented by Sequence ID No. 1;

(c) an amino acid sequence encoded by the nucleotide sequence of nucleotide's positions No. 1 to No. 1017 in the nucleotide sequence represented by Sequence ID No. 2;

(d) an amino acid sequence of a protein capable of converting acetophenone to an optically active 1-phenylethylamine in the presence of a racemic mixture of sec-butylamine, said amino acid sequence showing an amino acid identity with the amino acid sequence represented by Sequence ID No. 1 of 60% or higher;

(e) an amino acid sequence of a protein capable of converting acetophenone to an optically active 1-phenylethylamine in the presence of a racemic mixture of sec-butylamine and having a molecular weight of about 37 kDa as a monomer, said amino acid sequence showing an amino acid identity with the amino acid sequence represented by Sequence ID No. 1 of 80% or higher; and, (f) an amino acid sequence of a protein capable of converting acetophenone to an optically active 1-phenylethylamine in the presence of a racemic mixture of sec-butylamine and obtainable from a microorganism belonging to the genus Mycobacterium, said amino acid sequence showing an amino acid identity with the amino acid sequence represented by Sequence ID No. 1 of 60% or higher.

6. A gene having any of the following nucleotide sequences (hereinafter also referred to as "the gene of the present invention"):

(a) a nucleotide sequence of nucleotide's positions No. 1 to No. 1017 in the nucleotide sequence represented by Sequence ID No. 2; and, (b) a nucleotide sequence comprising a nucleotide substitution from adenine to guanine occurring at a position corresponding to nucleotide's position No.4 of a nucleotide sequence of nucleotide's positions No. 1 to 1017 in the nucleotide sequence represented by Sequence ID No. 2;

(c) a nucleotide sequence of about 1020 bp which is amplified by PCR using as primers an oligonucleotide having the nucleotide sequence of nucleotide's positions No. 1 to 28 in the nucleotide sequence represented by Sequence ID No. 2 or an oligonucleotide having the nucleotide sequence represented by Sequence ID No. 11, and an oligonucleotide having a complementary nucleotide sequence to the nucleotide sequence of nucleotide's positions No. 999 to 1020 in the nucleotide sequence represented by Sequence ID No. 2 and as a template a chromosome DNA derived from a microorganism belonging to the Mycobacterium and which encodes a protein capable of converting acetophenone to an optically active 1-phenylethylamine in the presence of a racemic mixture of sec-butylamine.

7. A gene having a nucleotide sequence of nucleotide's positions No. 1 to 1017 in the nucleotide sequence represented by Sequence ID No. 2.

8. A gene having a nucleotide sequence comprising a nucleotide substitution from adenine to guanine occurring at a position corresponding to nucleotide's position No.4 of a nucleotide sequence of nucleotide's positions No. 1 to 1017 in the nucleotide sequence represented by Sequence ID No. 2.

9. A gene formed by connecting a promoter capable of functioning in a host cell to the gene of the above 5 in a functional manner.

10. A vector containing the gene of the above 5 (hereinafter referred to as "the vector of the present invention").

11. A transformant obtainable by transducing the gene of the above 5 into a host cell (hereinafter referred to as "the transformant of the present invention").

12. A transformant obtainable by transducing the vector of the above 10 to a host cell.

13. The transformant according to the above 11 or the above 12, wherein the host cell is a microorganism cell.

14. A method for producing a transformant, comprising a step of transducing the gene of the above 5 or the vector of the above 10 into a host cell.

15. A method for producing a protein of the above 1, comprising a step of culturing a microorganism having the gene of the above 5.

16. The method according to the above 15, wherein said microorganism is the transformant of the above 11 or 12.

17. A method for producing an optically active amino compound represented by Formula (3):

$$X^1\text{—}C^*H(NH_2)\text{—}(CH_2)_m\text{—}R^1 \tag{3}$$

wherein $X^1$ is an optionally substituted $C_1$–$C_9$ alkyl group, an optionally substituted $C_6$–$C_{14}$ aryl group, an optionally substituted $C_7$–$C_{17}$ arylalkyl group, an optionally substituted $C_4$–$C_{12}$ heteroaryl group, an optionally substituted $C_5$–$C_{15}$ heteroarylalkyl group, an amino group, an aminocarbonyl group, a carboxyl group, a hydroxyl group, a thiol group, a guanidyl group, a cyano group, a halogen atom or a hydrogen atom, $R^1$ is a $C_1$–$C_6$ alkyl group, a carboxyl group, $C_2$–$C_6$ alkyloxycarbonyl group or a hydrogen atom, m is an integer of 0 to 6, and * is an asymmetric carbon atom with the proviso that said optically active amino compound represented by Formula (3) has the following structure represented by Formula (3a):

(3a)

when $R^1$ is a $C_1$–$C_6$ alkyl group or a hydrogen atom and said optically active amino compound represented by Formula (3) has the following structure represented by Formula (3b):

(3b)

when $R^1$ is a carboxyl group or $C_2$–$C_6$ alkyloxycarbonyl group, which comprises reacting a ketone compound represented by Formula (1):

$$X^1\text{—}CO\text{—}(CH_2)_m\text{—}R^1 \tag{1}$$

wherein $X^1$, $R^1$ and m have the meanings defined above, in the presence of an amino group-containing compound represented by Formula (2):

$$R^2\text{—}CH(NH_2)\text{—}R^3 \tag{2}$$

wherein $R^2$ is an optionally substituted $C_1$–$C_6$ alkyl group, an optionally substituted phenyl group or an optionally substituted $C_7$–$C_{10}$ phenylalkyl group, $R^3$ is a hydrogen atom, a $C_1$–6 alkyl group, a carboxyl group or a $C_2$–$C_5$ alkyloxycarbonyl group with the protein of the above 1 (hereinafter referred to as "Production Method 1 of the present invention").

18. The method according to the above 17, wherein $R^1$ of the ketone compound represented by Formula (1) is a carboxyl group.

19. The method according to the above 17, which is a method for producing an optically active amino compound represented by Formula (6):

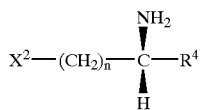
(6)

wherein $X^2$ is an optionally substituted phenyl group or an optionally substituted naphthyl group, $R^4$ is an $C_1$–$C_6$ alkyl group, and n is an integer of 0 to 4, which comprises reacting a ketone compound represented by Formula (4):

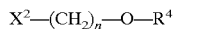
(4)

wherein $X^2$, $R^4$ and n have the meanings defined above in the presence of an amino group-containing compound represented by Formula (5):

(5)

wherein $R^5$ is an optionally substituted $C_1$–$C_6$ alkyl group, an optionally substituted phenyl group or an optionally substituted $C_7$–$C_{10}$ phenylalkyl group, $R^6$ is a hydrogen atom, a $C_1$–$C_6$ alkyl group, a carboxyl group or a $C_2$–$C_5$ alkyloxycarbonyl group, with the protein of the above 1 (hereinafter referred to as "Production Method 2 of the present invention").

20. The method according to the above 17, which is a method for producing an optically active amino compound represented by Formula (8):

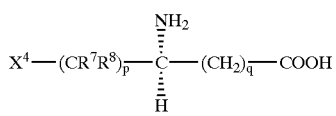
(8)

wherein $X^4$ is an optionally substituted $C_6$–$C_{14}$ aryl group, an optionally substituted $C_4$–$C_{12}$ heteroaryl group, an optionally substituted $C_1$–$C_3$ alkyl group, an amino group, an aminocarbonyl group, a hydroxyl group, a thiol group, a guanidyl group or a hydrogen atom, $R^7$ and $R^8$ may be the same or different and each is a hydrogen atom, a $C_1$–$C_3$ alkyl group or a hydroxyl group, p is an integer of 0 to 3 and q is an integer of 0 to 2, which comprises reacting a ketone compound represented by Formula (7)

(7)

wherein $X^4$, $R^7$, $R^8$, p and q have the meanings defined above in the presence of an amino group-containing compound represented by Formula (2):

(2)

wherein $R^2$ is an optionally substituted $C_1$–$C_6$ alkyl group, an optionally substituted phenyl group or an optionally substituted $C_7$–$C_{10}$ phenylaklyl group, $R^3$ is a hydrogen atom, a $C_1$–$C_6$ alkyl group, a carboxyl group or a $C_2$–$C_5$ alkyloxycarbonyl group, with the protein of the above 1 (hereinafter referred to as "Production Method 3 of the present invention").

21. A method for improving the ratio of an amino compound represented by Formula (9):

(9)

wherein $X^1$ is an optionally substituted $C_1$–$C_9$ alkyl group, an optionally substituted $C_6$–$C_{14}$ aryl group, an optionally substituted $C_7$–$C_{17}$ arylalkyl group, an optionally substituted $C_4$–$C_{12}$ heteroaryl group, an optionally substituted $C_5$–$C_{15}$ heteroarylalkyl group, an amino group, an aminocarbonyl group, a hydroxyl group, a thiol group, a guanidyl group, a cyano group, a halogen atom or a hydrogen atom, $R^1$ is a $C_1$–$C_6$ alkyl group, a carboxyl group, $C_2$–$C_6$ alkyloxycarbonyl group or a hydrogen atom, m is an integer of 0 to 6, and * is an asymmetric carbon atom with the proviso that said amino compound represented by Formula (9) has the following structure represented by Formula (9a):

(9a)

when $R^1$ is a $C_1$–$C_6$ alkyl group or a hydrogen atom and said optically active amino compound represented by Formula (9) has the following structure represented by Formula (9b):

(9b)

when $R^1$ is a carboxyl group or $C_2$–$C_6$ alkyloxycarbonyl group, which comprises reacting a ketone compound represented by Formula (14):

(14)

wherein $R^2$ is an optionally substituted $C_1$–$C_6$ alkyl group, an optionally substituted phenyl group or an optionally substituted $C_7$–$C_{10}$ phenylalkyl group, $R^3$ is a hydrogen atom, a $C_1$–$C_6$ alkyl group, a carboxyl group or a $C_2$–$C_5$ alkyloxycarbonyl group, in the presence of an amino group-containing compound represented by Formula (13):

(13)

wherein $X^1$, $R^1$ and m have the meanings defined above, with the protein of the above 1 (hereinafter referred to as "Improvement Method A of the present invention").

22. The method according to the above 21, which is a method for improving the ratio of an amino compound represented by Formula (12):

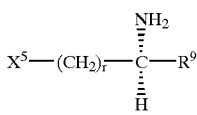  (12)

wherein $X^5$ is an optionally substituted phenyl group or an optionally substituted naphthyl group, $R^9$ is a $C_1$–$C_6$ alkyl group and r is an integer of 0 to 4, which comprises reacting an amino group-containing compound represented by Formula (10):

$$X^5\text{—}(CH_2)_r\text{—}CH(NH_2)\text{—}R^9 \quad (10)$$

wherein $X^5$, $R^9$ and r have the meanings defined above in the presence of a ketone compound represented by Formula (11):

$$R^{10}\text{—}CO\text{—}R^{11} \quad (11)$$

wherein $R^{10}$ is an optionally substituted $C_1$–$C_6$ alkyl group, an optionally substituted phenyl group or an optionally substituted $C_7$–$C_{10}$ phenylalkyl group, $R^{11}$ is a hydrogen atom, a $C_1$–$C_6$ alkyl group, a carboxyl group or a $C_2$–$C_5$ alkyloxycarbonyl group, with the protein of the above (hereinafter referred to as "Improvement Method B of the present invention").

Further scope of applicability of the present invention will become apparent from the detailed description given hereinafter. However, it should be understood that the detailed description and specific examples, while indicating preferred embodiments of the present invention, are given by way of illustration only, since various changes and modifications within the spirit and scope of the present invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer step or group of integers or steps but not the exclusion of any other integer or step or group of integer or step.

Sequence ID No. 6 is an oligonucleotide primer designed for PCR.

Sequence ID No. 7 is an oligonucleotide primer designed for PCR.

Sequence ID No. 8 is an oligonucleotide primer designed for PCR.

Sequence ID No. 9 is an oligonucleotide primer designed for PCR.

Sequence ID No. 10 is an oligonucleotide primer designed for PCR.

Sequence ID No. 11 is an oligonucleotide primer designed for PCR.

Sequence ID No. 12 is an oligonucleotide primer designed for PCR.

DETAILED DESCRIPTION OF THE INVENTION

The present invention is described in detail below.

A protein of the present invention includes a protein having any one of the following amino acid sequences:

(a) an amino acid sequence represented by Sequence ID No. 1;

(b) an amino acid sequence comprising an amino acid substitution occurring at a part corresponding to a part of an amino acid sequence represented by Sequence ID No. 1;

(c) an amino acid sequence of a protein capable of converting acetophenone to an optically active 1-phenylethylamine in the presence of a racemic mixture of sec-butylamine, said amino acid sequence showing an amino acid identity with the amino acid sequence represented by Sequence ID No. 1 of 60% or higher;

(d) an amino acid sequence of a protein capable of converting acetophenone to an optically active 1-phenylethylamine in the presence of a racemic mixture of sec-butylamine and having a molecular weight of about 37 kDa as a monomer, said amino acid sequence showing an amino acid identity with the amino acid sequence represented by Sequence ID No. 1 of 80% or higher; and, (e) an amino acid sequence of a protein capable of converting acetophenone to an optically active 1-phenylethylamine in the presence of a racemic mixture of sec-butylamine and derived from a microorganism belonging to the genus Mycobacterium, said amino acid sequence showing an amino acid identity with the amino acid sequence represented by Sequence ID No. 1 of 60% or higher. Typically, a protein having an amino acid sequence represented by Sequence ID No. 1, a protein having an amino acid sequence comprising an amino acid substitution from threonine to alanine occurring at a position corresponding to amino acid's position No.2 of an amino acid sequence represented by Sequence ID No. 1 and a protein having a molecular weight of about 37 kDa as a monomer which is obtainable from *Mycobacterium aurum* SC-S423 and which is capable of converting acetophenone to an optically active 1-phenylethylamine in the presence of a racemic mixture of sec-butylamine may be exemplified.

The amino acid sequence of the protein described above may be made short to a suitable length as long as it does not lose the ability of converting acetophenone into an optically active 1-phenylethylamine in the presence of a racemic mixture of sec-butylamine, and may for example be a protein having the amino acid sequence of amino acid's positions No. 23 to No. 339 in the amino acid sequence represented by Sequence ID No. 1.

The protein of the present invention has as an ability of catalyzing transamination stereoselectively at least an ability of converting acetophenone to an optically active 1-phenylethylamine in the presence of a racemic mixture of sec-butylamine. For example, 1 ml of 100 mM potassium phosphate buffer (pH 6.0) containing the protein of the present invention is supplemented with 400 mM (as a final concentration) racemic mixture of sec-butylamine, 10 mM (as a final concentration) acetophenone and 20 μM (as a final concentration) pyridoxal-5-phosphate (PLP) to obtain a reaction mixture which is kept at about 30 to 40° C. for about 2 hours to 4 days and then examined for the quantity of an optically active 1-phenylethylamine produced therein, whereby determining whether the ability described above is possessed or not. This procedure employs a method for quantifying an optically active 1-phenylethylamine which is exemplified in Examples described later.

Transamination catalyzed stereoselectively by the protein of the present invention may for example be a reaction wherein the ketone compound (1) is converted in the presence of the amino group-containing compound (2) into the optically active amino compound (3), a reaction wherein the ketone compound (4) is converted in the presence of the amino group-containing compound (5) into the optically active amino compound (6), a reaction wherein the ketone compound (7) is converted in the presence of the amino group-containing compound (2) into the optically active amino compound (8), a reaction wherein the ratio of the amino compound isomer (9) contained in the amino group-containing compound (13) is improved in the presence of the ketone compound (14), a reaction wherein the ratio of the optically active amino compound (12) contained in the amino group-containing compound (10) is improved in the presence of the ketone compound (11) and the like.

In the present invention, an amino acid identity with the amino acid sequence represented by Sequence ID No. 1 is a identity with the entire amino acid sequence represented by Sequence ID No. 1, and it is more preferred one in a case where the amino acid identity with the amino acid sequence of amino acid's positions No. 23 to No. 339 in Sequence ID No. 1 is higher. Typically, the amino acid identity is 80% or higher, more preferably 90% or higher, and particularly 95% or higher.

The gene of the present invention includes a gene encoding a protein having any one of the following amino acid sequences:

(a) an amino acid sequence represented by Sequence ID No. 1;

(b) an amino acid sequence comprising an amino acid substitution occurring at a part corresponding to a part of an amino acid sequence represented by Sequence ID No. 1;

(c) an amino acid sequence encoded by the nucleotide sequence of nucleotide's positions No. 1 to No. 1017 in the nucleotide sequence represented by Sequence ID No. 2;

(d) an amino acid sequence of a protein capable of converting acetophenone to an optically active 1-phenylethylamine in the presence of a racemic mixture of sec-butylamine, said amino acid sequence showing an amino acid identity with the amino acid sequence represented by Sequence ID No. 1 of 60% or higher;

(e) an amino acid sequence of a protein capable of converting acetophenone to an optically active 1-phenylethylamine in the presence of a racemic mixture of sec-butylamine and having a molecular weight of about 37 kDa as a monomer, said amino acid sequence showing an amino acid identity with the amino acid sequence represented by Sequence ID No. 1 of 80% or higher; and, (f) an amino acid sequence of a protein capable of converting acetophenone to an optically active 1-phenylethylamine in the presence of a racemic mixture of sec-butylamine and obtainable from a microorganism belonging to the genus Mycobacterium, said amino acid sequence showing an amino acid identity with the amino acid sequence represented by Sequence ID No. 1 of 60% or higher, and a gene having any of the following nucleotide sequences:

(a) a nucleotide sequence of nucleotide's positions No. 1 to No. 1017 in the nucleotide sequence represented by Sequence ID No. 2; and, (b) a nucleotide sequence comprising a nucleotide substitution from adenine to guanine occurring at a position corresponding to nucleotide's position No. 4 of a nucleotide sequence of nucleotide's positions No. 1 to 1017 in the nucleotide sequence represented by Sequence ID No. 2;

(c) a nucleotide sequence of about 1020 bp which is amplified by PCR using as primers an oligonucleotide having the nucleotide sequence of nucleotide's positions No. 1 to 28 in the nucleotide sequence represented by Sequence ID No. 2 or an oligonucleotide having the nucleotide sequence represented by Sequence ID No. 11, and an oligonucleotide having a complementary nucleotide sequence to the nucleotide sequence of nucleotide's positions No. 999 to 1020 in the nucleotide sequence represented by Sequence ID No. 2 and as a template a chromosome DNA derived from a microorganism belonging to the Mycobacterium and which encodes a protein capable of converting acetophenone to an optically active 1-phenylethylamine in the presence of a racemic mixture of sec-butylamine. Typically, a gene having a nucleotide sequence of nucleotide's positions No. 1 to 1017 in the nucleotide sequence represented by Sequence ID No. 2, and a gene having a nucleotide sequence comprising a nucleotide substitution from adenine to guanine occurring at a position corresponding to nucleotide's position No.4 of a nucleotide sequence of nucleotide's positions No. 1 to 1017 in the nucleotide sequence represented by Sequence ID No. 2 may be exemplified.

The gene described above may for example be a naturally-occurring gene, or a gene produced by mutagenizing into a naturally-occurring gene by means of a site directed mutaginesis or a randam mutagenesis.

For the purpose of searching a naturally-occurring gene, a microorganism capable of converting acetophenone in the presence of a racemic mixture of sec-butylamine into an optically active 1-phenylethylamine is subjected to an investigation, and those preferred to be investigated are microorganism belonging to the genus of Mycobacterium such as *Mycobacterium aurum, Mycobacterium neoaurum, Mycobacterium chubuense* and the like.

The gene of the present invention may be produced by a method exemplified below.

A chromosome DNA is prepared from a microorganism belonging to the genus of Mycobacterium such as *Mycobacterium aurum* strain SC-S423 [deposited under Budapest treaty with the accession number given by the following international depositary authority, FERM BP-7009 (original deposit dated Mar. 30, 1998) to National Institute of Bioscience and Human Technology Agency of Industrial Science and Technology in accordance with ordinary genetic engineering methods such as those described in "Molecular Cloning: A Laboratory Manual 2nd edition" (1989), Cold Spring Harbor Laboratory Press, "Current Protocols in Molecular Biology" (1987), John Wiley & Sons, Inc., and the like. Subsequently, the DNA prepared is used as a template in a polymerase chain reaction (hereinafter referred to as PCR) under the conditions specified below using as primers an oligonucleotide having the nucleotide sequence of nucleotide's position Nos. 1 to 28 in the nucleotide sequence represented by Sequence ID No. 2 or an oligonucleotide having the nucleotide sequence represented by Sequence ID No. 11 and an oligonucleotide having a complementary nucleotide sequence to the nucleotide sequence of nucleotide's positions Nos. 999 to 1020 in the nucleotide sequence represented by Sequence ID No. 2, whereby amplifying a DNA having a nucleotide sequence encoding the amino acid sequence represented by Sequence ID No. 1, or a DNA having a nucleotide sequence encoding an amino acid sequence in which one or more amino acids in the amino acid sequence represented by Sequence ID No. 1 are deleted, substituted, added or inserted.

In this procedure, the PCR may employ the conditions in which a reaction solution containing 4 dNTPs each at a final concentration of 200 µM, 2 primers described above each at a final concentration of 200 nM, TaqDNA polymerase and Pwo DNA polymerase at a total concentration of 26 mU/µl and a chromosome DNA employed as a template at a final concentration of 1 ng/µl is used and kept at 95° C. for 2 minutes and then subjected to 25 cycles in total, each cycle consisting of 15 seconds at 96° C. followed by 15 seconds at 60° C. followed by 1 minute at 72° C., and then kept at 72° C. for 10 minutes. An oligonucleotide employed as a primer in this PCR may appropriately be designed and synthesized based on the nucleotide sequence represented by Sequence ID No. 2 and subjected to the PCR in the conditions described above, whereby amplifying a DNA encoding a partial amino acid sequence of the amino acid sequence represented by Sequence ID No. 1, typically a DNA encoding the amino acid sequence of amino acid numbers 23 to 339 in the amino acid sequence represented by Sequence ID No. 1, or a DNA as a variant thereof in which one or more nucleotides in the nucleotide sequence are deleted, substituted, added or inserted. To the 5' terminal of the primer used in the PCR described above, an additional nucleotide sequence such as a restriction enzyme recognition sequence may be added. Typically, an oligonucleotide having a nucleotide sequence represented by Sequence ID No. 11 or 12 may be exemplified. When a DNA library formed by inserting a chromosome DNA or a cDNA into a vector is used as a template, an oligonucleotide having a nucleotide sequence selected from the nucleotide sequence encoding the amino acid sequence represented by Sequence ID No. 1 (e.g., an oligonucleotide having a nucleotide sequence of about 14 nucleotides or more from the 5' terminal of the nucleotide sequence encoding the amino acid sequence represented by Sequence ID No. 1) and an oligonucleotide of about 14 nucleotides or more having the complementary nucleotide sequence to a nucleotide sequence near the insertion site of the DNA in the vector employed for constructing the library are employed as primers to perform the PCR, whereby amplifying a DNA having a nucleotide sequence encoding the amino acid sequence represented by Sequence ID No. 1.

The DNA thus amplified can then be cloned into a vector in accordance with ordinary genetic engineering methods such as those described in "Molecular Cloning: A Laboratory Manual $2^{nd}$ edition" (1989), Cold Spring Harbor Laboratory Press, "Current Protocols in Molecular Biology" (1987), John Wiley & Sons, Inc., and the like. Typically, a plasmid vector pCRII available from Invitrogen or a plasmid vector pBluescript II available from Stratagene may for example be employed in the cloning.

The gene of the present invention may also be obtained by hybridizing a library of a chromosome DNA or a cDNA derived from a microorganism belonging to the genus of Mycobacterium with a DNA, as a probe, of about 15 nucleotides or more having a nucleotide sequence encoding the amino acid sequence represented by Sequence ID No. 1 in conditions described below followed by detecting a DNA to which such probe binds specifically.

A method for hybridize a library of a chromosome DNA or a cDNA with a probe may be a colony hybridization or a plaque hybridization, and it depends on the type of the vector employed in the preparation of the library. When the library employed is constructed using a plasmid vector, a colony hybridization is conducted. Typically, a library DNA is transduced into a microorganism enabling a replication of a plasmid vector employed in the preparation of the library to obtain a transformant which is then diluted and spread on an agar medium which is then incubated until colonies appear. When the library is prepared using a phage vector, then a plaque hybridization is performed. Typically, a microorganism enabling a replication of a phage vector employed in the preparation of the library is mixed with a library phage in the conditions allowing an infection to occur and then admixed further with a soft agar medium, which is then spread on an agar medium. Then the medium is incubated until plaques appear. In any of the procedures of the hybridization described above, a membrane is then mounted on the surface of the agar medium which has been incubated as described above to transfer a transformant or a phage onto the membrane. After treating this membrane with an alkali followed by a neutralization, the DNA is immobilized on the membrane. Typically, in the case of a plaque hybridization, the agar medium described above is covered with a nitrocellulose membrane or a nylon membrane, namely, Hybond-N' (Trade mark of Amersham), and allowed to stand for about 1 minutes, whereby allowing a phage particle to be adsorbed onto the membrane. Then the membrane is immersed in an alkaline solution (1.5 M sodium chloride, 0.5 N NaOH) for about 3 minutes to dissolve the phage particle to effect an elution of a phage DNA onto the membrane, followed by an immersion for about further 5 minutes in a neutralization solution (1.5 M sodium chloride, 0.5 M tris-HCl buffer, pH 7.5). After washing the membrane with a washing solution (0.3 M sodium chloride, 30 mM sodium citrate, 0.2 M tris-HCl buffer, pH 7.5) for about 5 minutes, a baking was effected, for example, at about 80° C. for about 90 minutes to immobilize the phage DNA onto the membrane.

The membrane thus prepared is then subjected to a hybridization using the DNA described above as a probe. The hybridization may for example be performed in accordance with the description in "Molecular Cloning: A Laboratory Manual $2^{nd}$ edition" (1989), Cold Spring Harbor Laboratory Press.

A DNA employed as a probe may be labeled with a radioactive isotope using a Random Labeling Kit available from Boehringer or TAKARA SHUZO Co., Ltd., and the labeling may also be effected by performing PCR using a probe DNA as a template with employing ($\alpha$-$^{32}$P)dCTP instead of a dCTP in an ordinary PCR reaction mixture. When a DNA used as a probe is labeled with a fluorescent dye, an ECL Direct Nucleic Acid Labeling and Detection System available from Amersham may for example be employed.

While variations of reagents and temperature conditions may be employed in a hybridization, a prehybridization solution containing 450 to 900 mM sodium chloride, 45 to 90 mM sodium citrate, together with 0.1 to 1.0% sodium dodecyl sulfate (hereinafter referred to as SDS), 0 to 200 µg/ml denaturated non-specific DNA, optionally with albumin, ficoll, polyvinylpyrrolidone each at a concentration of 0 to 0.2%, preferably a prehybridizaiton solution containing 900 mM sodium chloride, 90 mM sodium citrate, 1.0% SDS and 100 µg/ml denaturated calf-thymus DNA is provided in a volume of 50 to 200 µl of per 1 cm² of a membrane prepared as described above, and the membrane is immersed in this solution over a period of 1 to 4 hours at 42 to 65° C., preferably over 2 hours at 65° C. Then a hybridization solution containing 450 to 900 mM sodium chloride, 45 to 90 mM sodium citrate, together with 0.1 to 1.0% SDS, 0 to 200 μg/ml denaturated non-specific DNA, optionally with albumin, ficoll, polyvinylpyrrolidone each at a concentration of 0 to 0.2%, preferably a hybridization solution containing 900 mM sodium chloride, 90 mM sodium citrate, 1.0% SDS and 100 μg/ml denaturated calf-thymus DNA mixed with the probe prepared as described above (corresponding to $1.0\times10^4$ to $2.0\times10^6$ cpm per 1 cm$^2$ of the membrane) is provided in a volume of 50 to 200 μl of per 1 cm$^2$ of a membrane, and the membrane is immersed in this solution over a period of 12 to 20 hours at 42 to 65° C., preferably over 16 hours at 65° C., whereby effecting a hybridization.

After this hybridization, the membrane is taken out and washed for 15 minutes twice with a solution containing 15 to 300 mM sodium chloride, 1.5 to 30 mM sodium citrate and 0.1 to 1.0% SDS at 42 to 65° C., preferably with a solution containing 15 mM sodium chloride, 1.5 mM sodium citrate and 1.0% SDS at 65° C. Thereafter, the membrane is rinsed gently with 2×SSC solution (300 mM sodium chloride, 30 mM sodium citrate) and then dried. This membrane is subjected, for example, to an autoradiography to detect the location of the probe on the membrane, whereby detecting where the DNA which is hybridize with the probe employed is located on the membrane. A clone corresponding to the location of the detected DNA on the membrane is identified on the agar medium employed initially, and is picked up to isolate the clone having the relevant DNA.

The DNA obtained as described above can be cloned to a vector in accordance with ordinary genetic engineering methods such as those described in "Molecular Cloning: A Laboratory Manual 2$^{nd}$ edition" (1989), Cold Spring Harbor Laboratory Press, "Current Protocols in Molecular Biology" (1987), John Wiley & Sons, Inc., and the like. A vector which can be utilized may for example be pUC119 (TAKARA SHUZO Co., Ltd.), pTV118N (TAKARA SHUZO Co., Ltd.), pBluescriptII (Toyobo Co., Ltd.), pCRII-TOPO (Invitrogen), pTrc99A (Pharmacia), pKK331-1 (Pharmacia) and the like.

The nucleotide sequence of the DNA obtained as described above can for example be sequenced by a dideoxy terminator method described by F. Sanger, S. Nicklen and A. R. Coulson in "Proceeding of National Academy of Science, U.S.A. (1977)", 74:p5463–5467. A sample for sequencing of the nucleotide may be prepared also using a commercial reagent such as ABI PRISM Dye Terminator Cycle Sequencing Ready Reaction Kit available from Perkin Elmer.

A protein encoded by the DNA obtained as described above can be checked for its ability of catalyzing transamination stereoselectively by a method exemplified below. Thus, the relevant DNA is inserted into a vector as being connected downstream of the promoter capable of functioning in a host cell, and the vector is transduced into the host cell to obtain a transformant. Then, a culture of the transformant is reacted with a ketone compound (1) in the presence of an amino group-containing compound (2) to yield a reaction product, which is then analyzed. In this manner, a transformant having an ability of producing an optically active amino compound (3) predominantly can be identified, and such transformant is regarded to have a relevant gene encoding a protein having such ability. More typically, a culture of the transformant described above, for example, is suspended in a 100 mM potassium phosphate buffer (pH 6.0) containing 10 mM acetophenone, 400 mM racemic mixture of sec-butylamine and 20 μM pyridoxal-5-phosphate (PLP) to obtain a final volume of 1 ml, which is placed in a 1.5 ml sample tube, which is then incubated with shaking on a shaker at about 30° C. to about 40° C. for a period of about 2 hours to about 4 days. 200 μl of the suspension after this incubation was admixed with 400 μl of methanol and stirred and centrifuged at 10000×g for 5 minutes to obtain a supernatant, which is filtered to obrain a filtrate, which is analyzed by a gas chromatography or a high performance liquid chromatography (hereinafter referred to as HPLC) to quantify 1-phenylethylamine produced and to evaluate its optical purity, whereby judging whether the transformant has an optically active 1-phenylethylamine-producing ability as a representative ability of catalyzing transamination stereoselectively or not.

In order to express the gene of the present invention in a host cell, a gene consisting of a promoter capable of functioning in a host cell connected to the gene of the present invention in a functional manner, a vector containing the gene of the present invention is transduced into a host cell. The term "in a functional manner" referred herein means a condition in which when the gene of the present invention has been transduced into a host cell, the gene of the present invention is bound to a promoter in a manner enabling an expression under the regulation by the promoter. Such promoters may for example be a promoter of the lactose operon of E. coli, a promoter of the tryptophan operon of E. coli, or a synthetic promoter capable of functioning in an E. coli cell such as tac promoter or trc promoter. A promoter naturally corresponding to the gene of the present invention may also be employed. In general, the gene of the present invention which is connected in a functional manner to a promoter capable of functioning in a host cell is integrated in a vector such as those described above, which is then transduced into a host cell. Such vectors may for example be a vector containing a selection marker gene (e.g., antibiotic resistance-imparting gene such as kanamycin resistant gene, neomycin resistant gene) for the purpose of selecting a transformant into which the gene of the present invention is transduced based on a phenotype of such selection marker genes.

A host cell into which the gene of the present invention or the vector containing the gene of the present invention is transduced may for example be a cell of a microorganism classified in Escherichia, Bacillus, Corynebacterium, Staphylococcus, Streptomyces, Saccharomyces, Kluyveromyces, Aspergillus, Mycobacterium and the like. A method for transducing the gene of the present invention into a host cell may be any of those selected usually depending on the host cells, and may be, for example, a calcium chloride method described in "Molecular Cloning: A Laboratory Manual 2$^{nd}$ edition" (1989), Cold Spring Harbor Laboratory Press, "Current Protocols in Molecular Biology" (1987), John Wiley & Sons, Inc or an electroporation method described in "Methods in Electroporation: Gene Pulser/E. coli Pulser System", Bio-Rad Laboratories, (1993).

A transformant into which the gene of the present invention or the vector containing the gene of the present invention is transduced may be selected based on a phenotype of a selection marker gene contained in a vector into which the gene of the present invention is integrated as described above. To ensure that the transformant has the gene of the present invention or the vector containing the gene of the present invention, a DNA is prepared from the transformant and subjected to ordinary methods such as those described in "Molecular Cloning: A Laboratory Manual 2$^{nd}$ edition" (1989), Cold Spring Harbor Laboratory Press (restriction map identification, nucleotide sequencing, southern hybridization, western hybridization and the like).

The protein of the present invention may be prepared, for example, by culturing a microorganism having the gene of the present invention. Such microorganisms may be one capable of expressing the gene of the present invention and producing the protein of the present invention, such as, a wild strain which is isolated from environmental niches of a microorganism having the gene of the present invention, a variant derived from such wild strains by means of a treatment with a reagent or UV. Furthermore, the transformant obtained by transducing the gene of the present invention or the vector containing the gene of the present invention to a host cell may also be exemplified. More typically, *Mycohacterium aurum* strain SC-S432 which is a wild strain isolated by us may be exemplified. An *E. coli* obtained by transducing into a host cell the gene of the present invention connected in a functional manner to a tac promoter or a lac promoter, such as *E. coli* JM109/ptrc9 may also be exemplified.

A medium using for culturing a microorganism having the gene of the present invention as described above may be any of those employed usually for growing a microorganism which contains carbon sources and nitrogen sources, organic and inorganic salts as appropriate. Carbon sources may for example include saccharides such as glucose, fructose, sucrose, dextrin and the like, sugar alcohols such as glycerol, sorbitol and the like, organic acids such as fumaric acid, citric acid, pyruvic acid and the like. The amount of carbon sources listed above to be added to a medium is usually about 0.1% (w/v) to about 10% (w/v) based on a total amount of the medium.

Nitrogen sources may for example include ammonium salts of inorganic acids such as ammonium chloride, ammonium sulfate, ammonium phosphate and the like, ammonium salts of organic acids such as ammonium fumarate, ammonium citrate and the like, organic nitrogen sources such as meat extract, yeast extract, malt extract, soybean powder, corn steep liquor, cottonseed oil, dried yeast, casein hydrolysate and the like, as well as amino acids. Among those listed above, ammonium salts of organic acids, organic nitrogen sources and amino acids may mostly be employed also as carbon sources. The amount of nitrogen sources to be added is usually about 0.1% (w/v) to about 10% (w/v) based on the total amount of the medium.

Inorganic salts may for example be phosphates such as potassium phosphate, dipotassium phosphate, sodium phosphate, disodium phosphate and the like, chlorides such as potassium chloride, sodium chloride, cobalt chloride hexahydrate and the like, sulfates such as magnesium sulfate, ferrous sulfate heptahydrate, zinc sulfate heptahydrate, manganese sulfate trihydrate and the like, and the amount to be added is usually about 0.0001% (w/v) to about 1% (w/v) based on a total amount of the medium.

Alternatively, such mediums may previously be supplemented with a small amount of an amino compound such as the amino group-containing compounds or the optically active amino compounds used in the present invention, which may contribute to an increase in the production of the protein of the present invention by the microorganism described above, and an amino compound also serves as a nitrogen source and a carbon source for a cultivation of a microorganism described above. The amount of an amine to be added as described above is usually about 0.001% (w/v) or more, preferably about 0.01% (w/v) to 1% (w/v) based on a total amount of the medium.

In a case of a host cell into which a gene formed by connecting the gene of the present invention in a functional manner to a lactose-induced promoter, such as tac promoter, trc promoter, lac promoter and the like is transduced, an agent to induce the production of the protein of the present invention, such as isopropyl-β-D-thiogalactoside (IPTG), may be added to the medium described above.

A microorganism having the gene of the present invention can be cultivated in accordance with a method employed usually to culture a microorganism, including a liquid phase cultivation such as a rotatory shaking cultivation, a reciprocal shaking cultivation, a jar fermentation (Jar Fermenter cultivation) and a tank cultivation, or a solid phase cultivation. When a jar fermenter is employed, aseptic air should be introduced into the Jar Fermenter usually at an aeration rate of about 0.1 to about 2 times culture fluid volume per minute. The temperature at which the cultivation is performed may vary within a range allowing a microorganism to be grown, and usually ranges from about 15° C. to about 40° C., and the pH of the medium ranges from about 6 to about 8. The cultivation time may vary depending on the cultivation conditions, and is usually about 1 day to about 10 days.

The protein of the present invention, for instance produced by a microorganism having the gene of the present invention, may be used in various forms such as a culture of a microorganism producing the protein of the invention, a cell of a microorganism producing the protein of the present invention, a material obtained by treating such a cell, a cell free extract of a microorganism, a crudly purified protein, a purified protein and the like to produce an optically active amino compound. A material obtained by treating a cell described above includes for example a lyophilized cell, an acetone-dried cell, a ground cell, an autolysate of a cell, an ultrasonically treated cell, an alkali-treated cell, an organic solvent-treated cell and the like. Alternatively, the protein of the present invention in any of the various forms described above may be immobilized in accordance with known methods such as a support binding method employing an adsorption onto an inorganic support such as a silica gel or a ceramic, a cellulose or an ion exchange resin, as well as an inclusion method employing an enclosure in a polymeric matrix such as a polyacrylamide gel, a sulfur-containing polysaccharide gel (e.g., carrageenin gel), an alginic acid gel or an agar gel and then used in the production of an optically active amino compound.

As a method for purifying the protein of the present invention from a culture of a microorganism having the gene of the present invention may be used conventional methods employed in a purification of protein such as those exemplified below.

First, cells are harvested from a culture of a microorganism by centrifugation or an equivalent method, and then destroyed physically by an ultrasonic treatment, a DYNOM-ILL treatment or a FRENCH PRESS treatment or chemically by a surfactant or a cell-lyzing enzyme such as lysozyme. From the resultant suspension thus obtained, insoluble materials are removed using a membrane filter to prepare a cell-free extract, which is then fractionated by any appropriate means for separation and purification, such as a cation exchange chromatography, an anion exchange chromatography, a hydrophobic chromatography, a gel filtration chromatography and the like, whereby purifying the protein of the present invention. Supporting materials employed in such chromatography include for example a resin support such as cellulose, dextran and agarose connected with a carboxymethyl (CM) group, a diethylaminoethyl (DEAE) group, a phenyl group or a butyl group. A commercially available column already packed with any support such as Q-Sepharose FF, Phenyl-Sepharose HP (Trade Name, from Amersham Pharmacia Biotech), TSK-gel G3000SW (Trade Name, TOSOH CORPORATION) may also be employed.

A procedure for purifying the protein of the present invention is exemplified below.

Cells of a microorganism producing the protein of the present invention are harvested by centrifugation, and then suspended in a buffer such as 20 mM bis-tris propane/HCl buffer (pH 7.0). The suspension is treated ultrasonically for about 20 minutes to destroy the cells, and the resultant suspension thus obtained is centrifuged at about 13000×g for about 15 minutes to obtain a supernatant, which is then filtered through a membrane filter to remove insolubles to obtain a cell-free extract. The cell-free extract thus obtained is then loaded, for example, onto a Q Sepharose FF column (Trade Name, Amersham Pharmacia Biotech) and the column is eluted with a linear gradient of sodium chloride to obtain a series of fractions. A fraction containing the protein of the present invention is then loaded, for example, onto a Phenyl-Sepharose HP column (Trade Name, Amersham Pharmacia Biotech) and the column is eluted with a linear gradient of ammonium sulfate to obtain a series of fractions. A fraction containing the protein of the present invention is concentrated using a ultrafiltration membrane or equivalent, and then loaded, for example, onto a TSK-gel G3000 SW column (600 mm×7.5 mm ID) (Trade Name, TOSOH CORPORATION) and eluted, for example, with a 50 mM sodium phosphate buffer containing 0.15 M sodium chloride to obtain a series of fractions, whereby purifying the protein of the present invention. The fraction containing the protein of the present invention may be selected based, for example, on the ability of converting acetophenone to an optically active 1-phenylethylamine in the presence of a racemic mixture of sec-butylamine.

The optically active amino compound (3) can be obtained by reacting the protein of the present invention in the presence of the amino group-containing compound (2) with the ketone compound (1) (refered to as "Production Method 1" as descrbed above).

In the ketone compound (1), $X^1$ is an optionally substituted $C_1$–$C_9$ alkyl group ($C_1$–$C_9$ alkyl group, substituted $C_1$–$C_9$ alkyl group), an optionally substituted $C_6$–$C_{14}$ aryl group ($C_6$–$C_{14}$ aryl group, substituted $C_6$–$C_{14}$ aryl group), an optionally substituted $C_7$–$C_{17}$ arylalkyl group ($C_7$–$C_{17}$ arylalkyl group, substituted $C_7$–$C_{17}$ arylalkyl group), an optionally substituted $C_4$–$C_{12}$ heteroaryl group ($C_4$–$C_{12}$ heteroaryl group, substituted $C_4$–$C_{12}$ heteroaryl group), an optionally substituted $C_5$–$C_{15}$ heteroarylalkyl group ($C_5$–$C_{15}$ heteroarylalkyl group, substituted $C_5$–$C_{15}$ heteroarylalkyl group), an amino group, an aminocarbonyl group, a hydroxyl group, a thiol group, a guanidyl group, a cyano group, a halogen atom or a hydrogen atom. The term "substituted" used herein means that the group is substituted with the same or different substituents selected from a group consisting of a $C_1$–$C_3$ alkyl group, a $C_1$–$C_2$ haloalkyl group, a $C_1$–$C_2$ alkoxy group, a $C_1$–$C_2$ alkylthio group, a hydroxyl group, a cyano group, an amino group, a thiol group and a halogen atom in the proviso that the term "substituted" also means that the $C_6$–$C_{14}$ aryl group or the $C_4$–$C_{12}$ heteroaryl group is substituted with a carboxyl group. A preferred substituent may for example be methyl, ethyl, monochloromethyl, trifluoromethyl, methoxy, methylenedioxy, hydroxyl, cyano, amino and as well as fluorine, chlorine and bromine atoms.

$R^1$ may for example be a hydrogen atom, a straight or branched $C_1$–$C_6$ alkyl group such as methyl, ethyl, propyl groups; carboxyl group; a $C_2$–$C_5$ (straight or branched) alkyloxycarbonyl group such as methoxycarbonyl, ethoxycarbonyl, propyloxycarbonyl, butyloxycarbonyl groups.

In the amino group-containing compound (2), $R^2$ is an optionally substituted $C_1$–$C_6$ alkyl group ($C_1$–$C_6$ alkyl group, substituted $C_1$–$C_6$ alkyl group), an optionally substituted phenyl group (phenyl group, substituted phenyl group) and an optionally substituted $C_7$–$C_{10}$ phenylalkyl group ($C_7$–$C_{10}$ phenylalkyl group, substituted $C_7$–$C_{10}$ phenylalkyl group). The term "substituted" used herein means that the group is substituted with the same or different substituents selected from a group consisting of a $C_1$–$C_3$ alkyl group, a $C_1$–$C_2$ haloalkyl group, a $C_1$–$C_2$ alkoxy group, a hydroxyl group, a cyano group, an amino group, a carboxyl group, a methylthio group and a halogen atom. A preferred substituent may for example be methyl, ethyl, monochloromethyl, trifluoromethyl, methoxy, methylenedioxy, hydroxyl, cyano, amino and carboxyl groups as well as fluorine, chlorine and bromine atoms.

$R^3$ may for example be a hydrogen atom, a straight or branched $C_1$–$C_6$ alkyl group such as methyl, ethyl, propyl groups; carboxyl group; a $C_2$–$C_5$ (straight or branched) alkyloxycarbonyl group such as methoxycarbonyl, ethoxycarbonyl, propyloxycarbonyl, butyloxycarbonyl groups.

When the amino group-containing compound (2) has an asymmetric carbon atom, any of the optical isomers or a mixtures thereof may appropriately be selected and used. The amino group-containing compound (2) should be a compound different from the optically active amino compound (3) (herein, a compound different only in the stereoisomerism such as optical or geometrical isomerisms is not regarded to be a different compound). Thus, a combination of the amino group-containing compound (2) and an optically active amino compound (3) selected in Production Method 1 of the present invention never employs $R^2$ in the amino group-containing compound (2) which is identical to $X^1$ in the optically active amino compound (3) at the same time with $R^3$ in the amino group-containing compound (2) which is not identical to the —$(CH_2)m$—$R^1$ group in the optically active amino compound (3).

Production Method 1 of the present invention is performed usually in an aqueous buffer solution containing salts of inorganic acids such as an alkaline metal phosphate such as sodium phosphate and potassium phosphate or salts of organic acids such as an alkaline metal acetate such as sodium acetate and potassium acetate, and the concentrations of the ketone compound (1) and the amino group-containing compound (2) in a reaction mixture of Production Method 1 of the present invention are usually 30% (w/v) or lower, preferably 0.01 to 20% (w/v). The weight ratio of the amino group-containing compound (2) to the ketone compound (1) is usually 0.01 to 100, while the weight ratio of the amino group-containing compound (2) to the ketone compound (1) may be as relatively high as 10 to 100 for the purpose of an advantageous reaction rate and a higher yield of the optionally active amino compound (3). The amount of a protein of the present invention may vary depending on reaction time period and selectivity for the optically active amino compound (3) produced. When the protein of the present invention is used as a purified or crudely purified enzyme, the amount is usually 0.001 to 2 times that of the ketone compound (1), preferably 0.002 to 0.5 times, and when it is used as a culture of a microorganism, a non-treated or treated cell of a microorganism, then the amount is usually 0.01 to 200 times that of the ketone compound (1), preferably 0.1 to 50 times. The reaction temperature is usually 10 to 70° C., preferably 20 to 60° C. The pH of the reaction mixture is usually 4 to 12, preferably 5 to 11. The reaction time period may vary as desired, and is usually about 1 hour to 7 days.

A reaction system of Production Method 1 of the present invention may further contain an auxiliary agent such as a surfactant, a coenzyme and an organic solvent in order to reduce reaction time period and to increase a yield of the optically active amino compound (3), and such auxiliary agents may be added to a reaction mixture alone or in combination with each other as appropriate. The surfactant which may be used includes for example sodium dodecyl sulfate, polyethylene glycol mono-p-isooctylphenylether, cetylpyridinium bromide and the like, and the coenzyme includes for example a pyridoxal-5-phosphate (PLP) and the like. The organic solvent includes for example an alkane such as be n-heptane, cyclohexane and isooctane, an ether such as methyl-tert-butylether, an alcohol such as methanol, isopropanol and n-octanol, a sulfoxide such as DMSO and the like.

The optically active amino compound (3) obtained by Production Method 1 of the present invention may be recovered from a reaction mixture by known methods. For example, a culture of a microorganism or a treated or non-treated cell of such microorganism is separated from a reaction mixture by a centrifugation to obtain a supernatant, which are then applied to methods like ion-exchange chromatography to yield the optically active amino compound (3) or which is then made acidic and extracted with an organic solvent such as diethylether and toluene to remove an organic phase, and then an aqueous phase is made basic and extracted similarly with an organic solvent to remove an aqueous phase, and then the solvent is evaporated off under reduced pressure, and a further purification is performed if necessary, for example, by a distillation, to yield the optically active amino compound (3).

The optically active amino compound (6) is obtained by reacting the protein of the present invention in the presence of the amino group-containing compound (5) with the ketone compound (4) (referred to as "Production Method 2" as descrobed above).

In the ketone compound (4), $X^2$ is an optionally substituted phenyl group (phenyl group, substituted phenyl group), an optionally substituted naphthyl group (naphthyl group, substituted naphthyl group). The term "substituted" used herein means that one or more hydrogen atoms in a phenyl or naphthyl group, usually 1 to 2 hydrogen atoms of a phenyl group and 1 to 2 hydrogen atoms of a naphthyl group are substituted with the same or different substituents selected from a group consisting of a $C_1$–$C_3$ alkyl group, a $C_1$–$C_2$ haloalkyl group, a $C_1$–$C_2$ alkoxy group, a methylene dioxy group, a hydroxyl group, a cyano group, an amino group, a carboxyl group and a halogen atom. A preferred substituent may for example be methyl, ethyl, monochloromethyl, trifluoromethyl, methoxy, methylenedioxy, hydroxyl, cyano, amino and carboxyl groups as well as fluorine, chlorine and bromine atoms.

$R^4$ is a $C_1$–$C_6$ alkyl group, preferably a $C_1$–$C_3$ alkyl group, more preferably methyl and ethyl groups.

The ketone compound (4) may for example be acetophenone, 2-methoxyacetophenone, 3-methoxyacetophenone, 2,4-dichloroacetophenone, 3,4-dichloroacetophenone, 3-cyanoacetophenone, 4-hydroxyacetophenone, 4-methoxyacetophenone, 4-methylacetophenone, 4-chloroacetophenone, 1-(3,4-dimethoxyphenyl)propan-2-one, 1-(4-methoxyphenyl)propan-2-one, 1-(4-chlorophenyl)propan-2-one, 1-(4-hydroxyphenyl)propan-2-one, 1-(4-methylphenyl)propan-2-one, 1-(3,4-methylenedioxyphenyl)propan-2-one, 1-phenylpopan-1-one, α-acetonaphthone, β-acetonaphthone and the like.

$R^5$ in the amino group-containing compound (5) is an optionally substituted $C_1$–$C_6$ alkyl ($C_1$–$C_6$ alkyl, substituted $C_1$–$C_6$ alkyl group), an optionally substituted phenyl group (phenyl group, substituted phenyl group), an optionally substituted $C_7$–$C_{10}$ phenylalkyl group ($C_7$–$C_{10}$ phenylalkyl group, substituted $C_7$–$C_{10}$ phenylalkyl group) and the like.

A $C_1$–$C_6$ alkyl group may for example be a straight or branched $C_1$–$C_6$ alkyl group such as methyl, ethyl, propyl, butyl, 1-methylpropyl, 2-methylpropyl, pentyl, hexyl groups, and a $C_7$–$C_{10}$ phenylalkyl group may for example be a $C_7$–$C_{10}$ phenyl (straight or branched) alkyl group such as benzyl, 2-phenylethyl, 3-phenylpropyl, 4-phenylbutyl, α-methylbenzyl groups.

The term "substituted" used herein means that one or more hydrogen atoms in a $C_1$–$C_6$ alkyl group, a phenyl group or a $C_7$–$C_{10}$ phenylalkyl group, usually 1 to 2 hydrogen atoms of a $C_1$–$C_6$ alkyl group, 1 to 2 hydrogen atoms of a phenyl group or 1 to 3 hydrogen atoms of a $C_7$–$C_{10}$ phenylalkyl group are substituted with same or different substituents selected from a group consisting of a $C_1$–$C_3$ alkyl group, a $C_1$–$C_2$ haloalkyl group, a $C_1$–$C_2$ alkoxy group, a hydroxyl group, a cyano group, an amino group, a carboxyl group, a methylthio group and a halogen atom, preferably methyl, ethyl, monochloromethyl, trifluoromethyl, methoxy, methylenedioxy, hydroxyl, cyano, amino, carboxyl, methylthio groups and fluorine, chlorine and bromine atoms.

A substituted $C_1$–$C_6$ alkyl group may for example be carboxymethyl, carboxyethyl, 1-aminoethyl, 3-aminopropyl, 4-aminobutyl, hydroxymethyl, methylthioethyl groups, and a substituted phenyl group may for example be p-hydroxyophenyl, p-chlorophenyl, m,p-dihydoroxyphenyl groups, and a substituted $C_7$–$C_{10}$ phenylalkyl group may for example be p-hydroxyphenylethyl, p-chlorophenylmethyl, 1-phenyl-1-hydroxymethyl groups.

$R^6$ may for example be a hydrogen atom, a straight or branched $C_1$–$C_6$ alkyl group such as methyl, ethyl, propyl groups; carboxyl group; a $C_2$–$C_5$ (straight or branched) alkyloxycarbonyl group such as methoxycarbonyl, ethoxycarbonyl, propyloxycarbonyl, butyloxycarbonyl groups.

The amino group-containing compound (5) may for example be an α-amino acid such as alanine, phenylalanine, tyrosine, aspartic acid, glutamic acid, methionine, lysine, serine, leucine, isoleucine and phenylserine as well as their ($C_1$–$C_4$ alkyl) esters; an aliphatic amines such as propylamine, 1,2-diaminopropane, n-butylamine, sec-butylamine, 1,4-diaminobutane, 2-aminopentane, n-hexylamine and 2-aminoheptane; a phenylalkylamine such as 1-phenylethylamine, 2-phenylethylamine, benzylamine, 3-amino-1-phenylbutane and 4-amino-1-phenylpentane; an aminoalcohol such as 2-amino-1-propanol and the like. When the amino group-containing compound (5) has an asymmetric carbon atom, any of the optical isomers or a mixtures thereof may appropriately be selected and used. The amino group-containing compound (5) should be a compound different from the optically active amino compound (6) (herein a compound different only in the stereoisomerism such as optical or geometrical isomerisms is not regarded to be a different compound). Thus, a combination of the amino group-containing compound (5) and the optically active amino compound (6) selected in Production Method 2 of the present invention never employs $R^5$ in the amino group-containing compound (5) which is identical to the $X^2$—$(CH_2)_n$— group in the optically active amino compound (6) at the same time with $R^6$ in the amino group-containing compound (5) which is identical to $R^4$ in the optically active amino compound (6).

Production Method 2 of the present invention may be performed in the conditions described above with regard to Production Method 1.

The optically active amino compound (6) obtained by Production Method 2 of the present invention can be recovered from a reaction mixture by a known method. For example, a culture of a microorganism, as non-treated or treated, is separated by a centrifugation, which is then made acidic and extracted with an organic solvent such as diethylether and toluene to remove an organic phase, and then an aqueous phase is made basic and extracted similarly with an organic solvent to remove an aqueous phase, and then the solvent is evaporated off under reduced pressure, and a further purification is performed if necessary, for example, by a distillation, to yield the optically active amino compound (6).

An optically active amino compound (6) capable of being produced by Production Method 2 according to the present invention may be one having a steric configuration specified by Formula (6), such as those listed below.

1-Phenylethylamine, 1-(2-methoxyphenyl)ethylamine, 1-(3-methoxyphenyl)ethylamine, 1-(2,4-dichlorophenyl) ethylamine, 1-(3,4-dichlorophenyl)ethylamine, 1-(3-cyanophenyl)ethylamine, 1-(4-hydroxyphenyl)ethylamine, 1-(4-methoxyphenyl)ethylamine, 1-(4-methylphenyl) ethylamine, 1-(4-chlorophenyl)ethylamine, 1-(3,4-dimethoxyphenyl)-2-aminopropane, 1-(4-methoxyphenyl)-2-aminopropane, 1-(4-chlorophenyl)-2-aminopropane, 1-(4-hydroxyphenyl)-2-aminopropane, 1-(4-methylphenyl)-2-aminopropane, 1-(3,4-methylenedioxyphenyl)-2-aminopropane, 1-phenyl-1-aminopropane, 1-(α-naphthyl) ethylamine, 1-(β-naphthyl)ethylamine and the like.

The optically active amino compound (8) may be obtained by reacting the protein of the present invention in the presence of the amino group-containing compound (2) with the ketone compound (7) (referred to as "Production Method 3" as described above).

In the ketone compound (7), $X^4$ is an optionally substituted $C_6$–$C_{14}$ aryl group ($C_6$–$C_{14}$ aryl group, substituted $C_6$–$C_{14}$ aryl group), an optionally substituted $C_4$–$C_{12}$ heteroaryl group ($C_4$–$C_{12}$ heteroaryl group, substituted $C_4$–$C_{12}$ heteroaryl group), an optionally substituted $C_1$–$C_3$ alkyl group ($C_1$–$C_3$ alkyl group, substituted $C_1$–$C_3$ alkyl group), an amino group, an aminocarbonyl group, a hydroxyl group, a thiol group, a guanidyl group or a hydrogen atom.

The term "substituted" used herein means that one or more hydrogen atoms in the aryl group, the heteroaryl group or the alkyl group, usually 1 to 2 hydrogen atoms of a $C_6$–$C_{14}$ aryl group, 1 to 2 hydrogen atoms of a $C_4$–$C_{12}$ heteroaryl group, or 1 to 2 hydrogen atoms of a $C_1$–$C_3$ alkyl group are substituted with same or different substituents selected from a group consisting of a $C_1$–$C_3$ alkyl group, a $C_1$–$C_2$ haloalkyl group, a $C_1$–$C_2$ alkoxy group, a hydroxyl group, a cyano group, an amino group, a methylthio group and a halogen atom in the proviso that the term "substituted" also means that the $C_6$–$C_{14}$ aryl group or the $C_4$–$C_{12}$ heteroaryl group is substituted with a carboxyl group, preferably methyl, ethyl, monochloromethyl, trifluoromethyl, methoxy, methylenedioxy, hydroxyl, cyano, amino, methylthio groups as well as fluorine, chlorine and bromine atoms.

$R^7$ and $R^8$ may be the same or different and each represents a hydrogen atom, a $C_1$–$C_3$ alkyl group or a hydroxyl group.

A $C_1$–$C_3$ alkyl group may for example be methyl, ethyl, n-propyl and isopropyl groups.

P is an integer of 0 to 3 and q is an integer of 0 to 2.

A $C_6$–$C_{14}$ aryl group may for example be phenyl and naphthyl groups, and a $C_4$–$C_{12}$ heteroaryl group may for example be a heteroaromatic ring containing 1 or more sulfur atoms in its ring system such as 2-thienyl and 3-thienyl groups, a heteroaromatic ring containing 1 to more nitrogen atoms in its ring system such as 2-indolyl, 3-indolyl, 2-imidazolyl, 4-imidazolyl and 5-imidazolyl groups, and a $C_1$–$C_3$ alkyl group may for example be methyl, ethyl, n-propyl and isopropyl groups.

The ketone compound (7) may for example be pyruvic acid, β-hydroxypyruvic acid, 2-keto-3-mercaptopropionic acid, 2-keto-3-hydroxybutyric acid, 2-keto-4-(methylthio) butyric acid, 3-methyl-2-oxobutyric acid, 4-methyl-2-oxovaleric acid, 3-methyl-2-oxovaleric acid, trimethylpyruvic acid, phenylpyruvic acid, 4-chlorophenylpyruvic acid, 4-cyanophenylpyruvic acid, α-naphthylpyruvic acid, β-naphthylpyruvic acid, p-hydroxybenzoylformic acid, 2-keto-4-phenylbutyric acid, 3-(2-thienyl)pyruvic acid, 3-hydroxy-3-phenylpyruvic acid, 4-hydroxyphenylpyruvic acid, indole-3-pyruvic acid, oxaloacetic acid, 2-ketosuccinamic acid, α-ketoglutaric acid, 2-keto-5-amino-5-oxopentanoic acid, 2-keto-6-aminohexanoic acid, 2-keto-5-guanidinopentanoic acid, 2-keto-3-(4-imidazolyl) propionic acid, 2-ketobutyric acid, 3-ketobutyric acid, 3-keto-3-phenylpropionic acid and the like.

In Production Method 3 of the present invention, the amino group-containing compound (2) may be used in accordance with Production Method 1. However, it should be a compound different from the optically active amino compound (8) (herein, a compound different only in the stereoisomerism such as optical or geometrical isomerisms is not regarded to be a different compound). Thus, a combination of the amino group-containing compound (2) and the optically active amino compound (8) selected in Production Method 3 of the present invention never employs $R^2$ in the amino group-containing compound (2) which is identical to the $X^4$—$(CR^7R^8)_p$— group in the optically active amino compound (8) at the same time with $R^3$ in the amino group-containing compound (2) which is identical to the —$(CH_2)q$—COOH group in the optically active amino compound (8).

Production Method 3 of the present invention may be performed in the conditions described above with regard to Production Method 1.

The optically active amino compound (8) produced by Production Method 3 may be one having a steric configuration specified by Formula (8), such as those listed below.

α-amino acid such as alanine, serine, cysteine, threonine, methionine, valine, leucine, isoleucine, tert-leucine, phenylalanine, p-chlorophenylalanine, p-cyanophenylalanine, α-naphthylalanine, β-naphthylalanine, p-hydroxyphenylglycine, homophenylalanine, 3-(2-thienyl)alanine, phenylserine, tyrosine, tryptophane, aspartic acid, asparagine, glutamic acid, glutamine, lysine and arginine, histidine, 2-aminobutyric acid, β-amino acid such as 3-aminobutyric acid and 3-amino-3-phenylpropionic acid and the like.

The ratio of the amino compound isomer (9) may be increased by reacting the protein of the present invention in the presence of the ketone compound (14) with the amino group-containing compound (13) (referred to as "Improvement Method A" as described above).

The expression that the ratio of the amino compound isomer (9) is increased in Improving Method A of the present invention means that the ratio of the amino compound isomer (9) to another isomer other than the amino compound isomer (9) in the two optical isomers on the basis of an asymmetric carbon atom bound to the amino group in an amino group-containing compound (13) is increased.

In the ketone compound (14), $R^2$ is an optionally substituted $C_1$–$C_6$ alkyl group ($C_1$–$C_6$ alkyl group, substituted $C_1$–$C_6$ alkyl group, an optionally substituted phenyl group (phenyl group, substituted phenyl group) and an optionally substituted $C_7$–$C_{10}$ phenylalkyl group ($C_7$–$C_{10}$ phenylalkyl group, substituted $C_7$–$C_{10}$ phenylalkyl group). The term "substituted" used herein means that a group is substituted with the same or different substituents selected from a group consisting of a $C_1$–$C_3$ alkyl group, a $C_1$–$C_2$ haloalkyl group, a $C_1$–$C_2$ alkoxy group, a hydroxyl group, a cyano group, an amino group, a carboxyl group, a methylthio group and a halogen atom. A preferred substituent may for example be methyl, ethyl, monochloromethyl, trifluoromethyl, methoxy, methylenedioxy, hydroxyl, cyano, amino and carboxyl groups as well as fluorine, chlorine and bromine atoms.

$R^3$ may for example be a hydrogen atom, a straight or branched $C_1$–$C_6$ alkyl group such as methyl, ethyl, propyl groups; carboxyl group; a $C_2$–$C_5$ (straight or branched) alkyloxycarbonyl group such as methoxycarbonyl, ethoxycarbonyl, propyloxycarbonyl, butyloxycarbonyl groups.

In the amino group-containing compound (13), $X^1$ is an optionally substituted $C_1$–$C_9$ alkyl group ($C_1$–$C_9$ alkyl group, substituted $C_1$–$C_9$ alkyl group), an optionally substituted $C_6$–$C_{14}$ aryl group ($C_6$–$C_{14}$ aryl group, substituted $C_6$–$C_{14}$ aryl group), an optionally substituted $C_7$–$C_{17}$ arylalkyl group ($C_7$–$C_{17}$ arylalkyl group, substituted $C_7$–$C_{17}$ arylalkyl group), an optionally substituted $C_4$–$C_{12}$ heteroaryl group ($C_4$–$C_{12}$ heteroaryl group, substituted $C_4$–$C_{12}$ heteroaryl group), an optionally substituted $C_5$–$C_{15}$ heteroarylalkyl group ($C_5$–$C_{15}$ heteroarylalkyl group, substituted $C_5$–$C_{15}$ heteroarylalkyl group), an amino group, an aminocarbonyl group, a hydroxyl group, a thiol group, a guanidyl group, a cyano group, a halogen atom or a hydrogen atom. The term "substituted" used herein means that a group is substituted with same or different substituents selected from a group consisting of a $C_1$–$C_3$ alkyl group, a $C_1$–$C_2$ haloalkyl group, a $C_1$–$C_2$ alkoxy group, a $C_1$–$C_2$ alkylthio group, a hydroxyl group, a cyano group, an amino group, a thiol group and a halogen atom in the proviso that the term "substituted" also means that the $C_6$–$C_{14}$ aryl group or the $C_4$–$C_{12}$ heteroaryl group is substituted with a carboxyl group. A preferred substituent may for example be methyl, ethyl, monochloromethyl, trifluoromethyl, methoxy, methylenedioxy, hydroxyl, cyano, amino and methylthio groups as well as fluorine, chlorine and bromine atoms.

While the ratio of the optical isomers of the amino group-containing compound (13) employed as a starting material in Improvement Method A of the present invention is not particularly limited, it is advantageous industrially to use a racemic mixture of the amino group-containing compound (13) since such amino group-containing compound (13) is available frequently as a racemic mixture.

Improvement Method A of the present invention is performed usually in an aqueous buffer solution containing salts of inorganic acids such as an alkaline metal phosphate such as sodium phosphate and potassium phosphate and salts of organic acids such as an alkaline metal acetate such as sodium acetate and potassium acetate, and concentrations of the ketone compound (14) and the amino group-containing compound (13) in a reaction mixture of Improvement Method A of the present invention are usually 30% (w/v) or lower, preferably 0.01 to 20% (w/v). The weight ratio of the ketone compound (14) to the amino group-containing compound (13) is usually 0.01 to 100, while the weight ratio of a ketone compound (14) to the amino group-containing compound (13) may be as relatively high as 1 to 10 for the purpose of an advantageous reaction rate and a higher yield of the amino compound isomer (9). The amount of the protein of the present invention may vary depending on reaction time period and selectivity for the amino compound isomer (9) produced. When the protein of the present invention is used as a purified or crudely purified enzyme, the amount is usually 0.001 to 2 times that of the amino group-containing compound (13), preferably 0.002 to 0.5 times, and when it is used as a culture of a microorganism, a non-treated or treated cell of a microorganism then the amount is usually 0.01 to 200 times that of the amino group-containing compound (13), preferably 0.1 to 50 times. The reaction temperature is usually 10 to 70° C., preferably 20 to 60° C. The pH of the reaction mixture is usually 4 to 12, preferably 5 to 11. The reaction time period may vary as desired. The longer the reaction time becomes, the higher the isomer ratio of an amino compound becomes and the result makes that the optical purity is improved. It may be for example about 1 hour to 7 days.

A reaction system of Improvement Method A of the present invention may further contain an auxiliary agent such as a surfactant, a coenzyme and an organic solvent in order to reduce reaction time period and to increase a yield of the amino compound isomer (9), and such auxiliary agents may be added to a reaction mixture alone or in combination with each other as appropriate. The surfactant which may be used may for example be sodium dodecylsulfate, polyethylene glycol mono-p-isooctylphenylether, cetylpyridinium bromide and the like, and the coenzyme may for example be a pyridoxal-5-phosphate (PLP) and the like. The organic solvent may for example be an alkane such as be n-heptane, cyclohexane and isooctane, an ether such as methyl-tert-butylether, an alcohol such as methanol, isopropanol and n-octanol, a sulfoxide such as DMSO and the like.

The amino compound isomer (9) obtained by Improvement Method A of the present invention may be recovered from a reaction mixture by known methods. For example, a culture of a microorganism or a treated or non-treated cell of such microorganism is separated from a reaction mixture by a centrifugation to obtain a supernatant, which are then applied to methods like ion-exchange chromatography to yield the amino compound isomer (9) or which is then made acidic and extracted with an organic solvent such as diethylether and toluene to remove an organic phase, and then an aqueous phase is made basic and extracted similarly with an organic solvent to remove an aqueous phase, and then the solvent is evaporated off under reduced pressure, and a further purification is performed if necessary, for example, by a distillation, to yield the amino compound isomer (9).

The ratio of the amino compound isomer (12) may be increased by reacting the protein of the present invention in the presence of the ketone compound (11) with the amino group-containing compound (10) (hereinafter referred to as Improvement Method B of the present invention).

In the amino group-containing compound (10), $X^5$ is an optionally substituted phenyl group (phenyl group, substituted phenyl group), an optionally substituted naphthyl group (naphthyl group, substituted naphthyl group). The term "substituted" used herein means that one or more hydrogen atoms in the phenyl or the naphthyl group, usually 1 to 2 hydrogen atoms of a phenyl group and 1 to 2 hydrogen atoms of a naphthyl group are substituted with same or different substituents selected from a group consisting of a $C_1$–$C_3$ alkyl group, a $C_1$–$C_2$ haloalkyl group, a $C_1$–$C_2$ alkoxy group, a methylene dioxy group, a hydroxyl group, a cyano group, an amino group, a carboxyl group and a halogen atom. A preferred substituent may for example be methyl, ethyl, monochloromethyl, trifluoromethyl, methoxy, methylenedioxy, hydroxyl, cyano, amino and carboxyl groups as well as fluorine, chlorine and bromine atoms.

$R^9$ is a $C_1$–$C_6$ alkyl group, preferably a $C_1$–$C_3$ alkyl group, more preferably methyl and ethyl groups.

The amino group-containing compound (10) may for example be 1-phenylethylamine, 1-(2-methoxyphenyl)ethylamine, 1-(3-methoxyphenyl)ethylamine, 1-(2,4-dichlorophenyl)ethylamine, 1-(3,4-dichlorophenyl)ethylamine, 1-(3-cyanophenyl)ethylamine, 1-(4-hydroxyphenyl)ethylamine, 1-(4-methoxyphenyl)ethylamine, 1-(4-methylphenyl)ethylamine, 1-(4-chlorophenyl)ethylamine, 1-(3,4-dimethoxyphenyl)-2-aminopropane, 1-(4-methoxyphenyl)-2-aminopropane, 1-(4-chlorophenyl)-2-aminopropane, 1-(4-hydroxyphenyl)-2-aminopropane, 1-(4-methylphenyl)-2-aminopropane, 1-(3,4-merhylenedioxyphenyl)-2-aminopropane, 1-phenyl-1-aminopropane, 1-(α-naphthyl)ethylamine, 1-(β-naphthyl)ethylamine and the like.

While the ratio of the optical isomers of the amino group-containing compound (10) employed as a starting material in Improvement Method B of the present invention is not particularly limited, it is advantageous industrially to use a racemic mixture of the amino group-containing compound (10) since such amino group-containing compound (10) is available frequently as a racemic mixture.

$R^{10}$ in the ketone compound (11) is an optionally substituted $C_1$–$C_6$ alkyl group ($C_1$–$C_6$ alkyl group, substituted $C_1$–$C_6$ alkyl group), an optionally substituted phenyl group (phenyl group, substituted phenyl group) and an optionally substituted $C_7$–$C_{10}$ phenylalkyl group ($C_7$–$C_{10}$ phenylalkyl group, substituted $C_7$–$C_{10}$ phenylalkyl group).

The term "substituted" used herein means that one or more hydrogen atoms in the $C_1$–$C_6$ alkyl group, the phenyl group or the $C_7$–$C_{10}$ phenylalkyl group, usually 1 to 2 hydrogen atoms of a $C_1$–$C_6$ alkyl group, 1 to 2 hydrogen atoms of a phenyl group or 1 to 3 hydrogen atoms of a $C_7$–$C_{10}$ phenylalkyl group are substituted with same or different substituents selected from a group for example consisting of a $C_1$–$C_3$ alkyl group, a $C_1$–$C_2$ haloalkyl group, a $C_1$–$C_2$ alkoxy group, a hydroxyl group, a cyano group, an amino group, a carboxyl group, a methylthio group and a halogen atom, preferably methyl, ethyl, monochloromethyl, trifluoromethyl, methoxy, methylenedioxy, hydroxyl, cyano, amino, carboxyl, methylthio groups and fluorine, chlorine and bromine atoms.

A $C_1$–$C_6$ alkyl group may for example be a straight or branched $C_1$–$C_6$ alkyl group such as methyl, ethyl, propyl, butyl, 1-methylpropyl, 2-methylpropyl, pentyl, hexyl groups, and a $C_7$–$C_{10}$ phenylalkyl group may be a $C_7$–$C_{10}$ phenyl (straight or branched) alkyl group such as benzyl, 2-phenylethyl, 3-phenylpropyl, 4-phenylbutyl, α-methylbenzyl groups.

A substituted $C_1$–$C_6$ alkyl group may for example be carboxymethyl, carboxyethyl, 1-aminoethyl, 3-aminopropyl, 4-aminobutyl, hydroxymethyl, methylthioethyl groups, and a substituted phenyl group may for example be p-hydroxyphenyl, p-chlorophenyl, m,p-dihydroxyphenyl groups, and a substituted $C_7$–$C_{10}$ phenylalkyl group may be p-hydroxyphenylethyl, p-chlorophenylmethyl, 1-phenyl-1-hydroxymethyl groups.

$R^{11}$ may be a hydrogen atom, a straight or branched $C_1$–$C_6$ alkyl group such as methyl, ethyl, propyl groups; carboxyl group; a $C_2$–$C_5$ (straight or branched) alkyloxycarbonyl group such as methoxycarbonyl, ethoxycarbonyl, propyloxycarbonyl, butyloxycarbonyl groups.

The ketone compound (11) may for example be a ketone such as acetone and 2-butanone, an aldehyde such as propionaldehyde and benzaldehyde, the keto acid such as oxaloacetic acid, pyruvic acid and α-ketobutyric acid, an alkali metal salt of the keto acid described above such as sodium pyruvate and an alkyl ester of a keto acid such as methyl pyruvate and the like.

Improvement Method B of the present invention may be performed in conditions similar to those described above with regard to Improvement Method A.

It is contemplated that the ratio of an amino compound isomer (12) to the isomer other than the amino compound isomer (12) obtained by Improvement Method B is increased.

EXAMPLES

The present invention is further described in the following Examples, which are not intended to restrict the scope of the present invention.

Quantitative analysis of the optically active amino compound in Examples 1 to 8 was performed by a gas chromatography under a condition described below in Section (1), while determination of optical purity of the amino compound was performed by HPLC under a condition described below in Section (2). The quantitative analysis and the determination of optical purity of the optically active amino compounds in Examples 12 to 15 were performed, after derivatization described below in Section (3), by HPLC under a condition described below in Section (4).

(1) Quantitative Analysis of Amino Compound (Gas Chromatography)

Column: DB-17 (inner diameter: 0.25 mm, coating thickness: 0.25 μm, length: 30 m, J&W)

Column condition: Temperature is raised from 80° C. to 250° C. (rate: 5° C./min).

Detector: FID (Detection temperature: 250° C.)

(2) Determination of Optical Purity of Amino Compound (HPLC)

Column: OA-4100 or OA-4800 (SUMIKA CHEMICAL ANALYSIS SERVICE, LTD)

Mobile phase: n-Hexane:ethanol:trifluoroacetic acid=240:10:1

Detection wavelength: 254 nm (3) Amino Compound Derivatization

50 μl of a reaction mixture is combined with 100 μl of 4 mg/ml solution of 2,3,4,6-tetra-O-acetyl β-glucopyranosyl isothiocyanate (GITC, WAKO PURE CHEMICAL INDUSTRIES, LTD) in acetonitrile and 50 μl of 2 mg/ml solution of triethylamine in acetonitrile and allowed to stand at 30° C. for 30 minutes. The mixture is filtered through a 0.2 μm filter to obtain a filtrate, which is used as a sample for an HPLC.

(4) Quantitative Analysis and Determination of Optical Purity of Amino Compound (HPLC)

Column: SUMIPACKS ODS L-03-4615 (SUMIKA CHEMICAL ANALYSIS SERVICE, LTD)

Column temperature: 35° C.

Flow rate: 1 ml/min

Detection wavelength: UV254 nm

Eluent A: 20 mM $KH_2PO_4$ (pH 3.7)

Eluent B: Acetonitrile
Eluting condition: The ratio of B in the eluent varies from 10% to 60% depending on analytes.

Example 1

(Purification of the Protein of the Present Invention)

(1) A 500 mL Sakaguchi flask containing 100 ml of sterilized medium (pH 7.0) containing 0.2% (w/v) glycerol, 0.1% (w/v) sodium pyruvate, 0.2% (w/v) (R)-1-phenylethylamine, 0.45% (w/v) dipotassium phosphate, 0.3% (w/v) potassium phosphate, 0.01% (w/v) magnesium sulfate, 0.0001% (w/v) ferrous sulfate heptahydrate, 0.0001% (w/v) zinc sulfate heptahydrate, 0.0001% (w/v) manganese sulfate trihydrate an d 0.0001% (w/v) cobalt chloride hexahydrate was inoculated with 1 mL of a culture of *Mycobacterium aurum* strain SC-S423 which had previously been cultivated in a medium of the similar composition, and incubated at 30° C. for 7 days with reciprocal shaking. 4 L of the culture thus obtained was centrifuged (10,000 G, 10 minutes) to harvest cells, and the wet cells thus obtained were washed twice with 100 mL of 100 mM potassium phosphate buffer (pH 7.0) to obtain 18 g of the wet cells.

(2) 16 g of the wet cells thus obtained were suspended in 60 ml of 20 mM bis-tris propane/HCl buffer (pH 7.0) containing 20 µM pyridoxal-5-phosphate (PLP). The suspension was distrusted by sonication for 20 minutes (SONIFIER, Trade Mark of Branson Sonic Power) and then centrifuged (at 13,000 G for 15 minutes) to remove cell debris. The resultant supernatant was filtered through a membrane filter (0.45 µm) to obtain a filtrate, which was used as a cell-free extract. This cell-free extract was applied onto a Q Sepharose FF column (26 mmφ×10 cm, Amersham Pharmacia Biotech) and eluted with a linear gradient of sodium chloride (gradient rate: 0.01 M/min, concentration of sodium chloride: from 0 M to 0.6 M, flow rate: 8 ml/min) in 20 mM bis-tris propane/HCl buffer (pH 7.0). A 80 ml fraction eluted over 0.35 M to 0.45 M sodium chloride was collected. A 63 ml of this fraction was supplemented with ammonium sulfate at a final concentration of 0.8 M, and loaded onto a Phenyl-Sepharose HP column (16 mmφ×10 cm, Amersham Pharmacia Biotech) and eluted with a linear gradient of ammonium sulfate (gradient rate: 0.008 M/min, concentration of ammonium sulfate: from 0.8 M to 0 M, flow rate: 3 ml/min) in 20 mM bis-tris propane/HCl buffer (pH 7.0). A 24 ml fraction eluted over 0.4 M to 0.35 M ammonium sulfate was collected and used as a enzyme solution.

(3) The enzyme solution obtained as described in Section (2) was analyzed by a SDS-polyacrylamide gel electrophoresis (Gel: PhastGel Gradient 10–15, Buffer strip: PhastGel SDS buffer strip, system: Phast System, all from Amersham Pharmacia Biotech), which indicated almost a single band. Furthermore, the enzyme solution was loaded onto a gel filtration column TSK-gel G3000SW (600 mm×7.5 mmID, Tosoh Corporation) and eluted with 50 mM soduim phosphate buffer (pH 7.0) containing 0.15M sodium chloride. As a result, an activity to produce an optically active amino compound was detected in a fraction eluted at a position showing Molecular Weight about 310 kDa.

Example 2

200 µl of the enzyme solution obtained in Example 1 was diluted with 200 µl of 0.1M potassium phosphate buffer (pH 6.0) and added to 800 µl of a 0.1 M potassium phosphate buffer (pH 6.0) solution containing 10 µmoles of acetophenone, 100 µmoles of a racemic mixture of sec-butylamine and 0.02 µmoles of pyridoxal-5-phosphate (PLP) and the mixture was kept at 40° C. for 71 hours. After this period, an optically active amino compound in the reaction mixture was quantified. The results indicated that a yield of 1-phenylethylamine was 19.9% with the optical isomer ratio of the R form being 100%.

Example 3

200 µl of the enzyme solution obtained in Example 1 was diluted with 200 µl of 0.1M potassium phosphate buffer (pH 6.0) and added to 800 µl of a 0.1 M potassium phosphate buffer (pH 6.0) solution containing 10 µmoles of acetophenone, 100 µmoles of D-alanine and 0.02 µmoles of pyridoxal-5-phosphate (PLP) and the mixture was kept at 40° C. for 3 hours. Subsequently, an aliquot of the reaction mixture was subjected to the quantification of amino compound. The results indicated that a yield of 1-phenylethylamine was 2.6% with the optical isomer ratio of the R form being 100%.

Example 4

360 µl of 0.1 M potassium phosphate buffer (pH 6) containing 5 µmoles of a racemic mixture of amino compounds shown in Table 1, 10 µmoles of sodium pyruvate and 0.01 µmoles of pyridixal-5-phosphate (PLP) was combined with 140 µl of the enzyme solution obtained in Example 1 when using 1-phenylethylamine as a racemic mixture of amino compound, or combined with 140 µl of the enzyme solution obtained in Example 1 which had been subjected to a 2-fold dilution with 0.1 M potassium phosphate buffer (pH 6) when using 1-(3,4-dichlorophenyl)-ethylamine or 1-(3,4-dimethoxyphenyl)-2-aminopropane, and the mixture was reacted at 40° C. for 1 hour. The optical isomer ratio of the amino compound remaining in the reaction mixture was examined. The results are shown in Table 1.

TABLE 1

| Amino compound | Optical isomer ratio (R/S) of amino compound after reaction |
|---|---|
| 1-Phenylethylamine | 0/100 |
| 1-(3,4-Dichlorophenyl)-ethylamine | 31/69 |
| 1-(3,4-Dimethoxyphenyl)-2-aminopropane | 44/56 |

Example 5

(1) A 500 mL Sakaguchi flask containing 100 ml of a sterilized medium containing 0.2% (w/v) glycerol, 0.1% (w/v) sodium pyruvate, 0.2% (w/v) (R)-1-phenylethylamine, 0.45% (w/v) dipotassium phosphate, 0.3% (w/v) potassium phosphate, 0.01% (w/v) magnesium sulfate, 0.0001% (w/v) ferrous sulfate heptahydrate, 0.0001% (w/v) zinc sulfate heptahydrate, 0.0001% (w/v) manganese sulfate trihydrate and 0.0001% (w/v) cobalt chloride hexahydrate was inoculated with 1 mL of a culture of *Mycobacterium aurum* strain SC-S423 which had previously been cultivated in a medium of the similar composition, and incubated at 30° C. for 7 days with reciprocal shaking.

(2) The culture thus obtained was centrifuged (10,000 G, 10 minutes) to collect wet cells.

(3) The wet cells thus obtained were suspended in 2 mL of 100 mM glycine buffer (pH 9.0). 1260 pL of a 0.2% (v/v) aqueous solution (pH 9.0) of 1-phenylethylamine as a racemic mixture was combined with 200 μL of a 2.2% (w/v) aqueous solution of sodium pyruvate, 440 μL of 100 mM glycine buffer (pH 9.0) and 100 μL of the cell suspension obtained as described above, and incubated at 30° C. for 21.5 hours. An aliquot of the reaction mixture was combined with a doubled volume of methanol and stirred thoroughly and centrifuged to remove the cell and recover a supernatant which was then subjected to a gas chromatography, which indicated that 54% of 1-phenylethylamine was lost. The remaining reaction mixture was adjusted at pH 12 with an aqueous solution of sodium hydroxide and then the residual 1-phenylethylamine was extracted into diethylether. The optical purity of 1-phenylethylamine in the extract was determined by HPLC and the results indicated that the ratio of (R)-form/(S)-form was 0/100.

Example 6

(1) 1 L from a culture obtained by a cultivation of ten 500 mL Sakaguchi flasks in the manner similar to that in Section (1) of Example 5 was centrifuged (10,000 G, 10 minutes) to collect cells, and the wet cells obtained were suspended in 50 mL of distilled water.

(2) 630 μL of an aqueous solution of 1-phenylethylamine as a racemic mixture obtained by dissolving 200 μL of 1-phenylethylamine as a racemic mixture and 900 μL of 2N aqueous solution of sulfuric acid in 100 ml of distilled water was combined with 100 μL of a 2.2% (w/v) aqueous solution of sodium pyruvate and further combined with 100 μL of 1 M buffer at any one of various pHs (employing citrate buffer at pH 5 to 6, potassium phosphate buffer at pH 6 to 8, tris-HCl buffer at pH 8 to 9, glycine buffer at pH 9 to 10, carbonate buffer at pH 11) and 70 μL of distilled water, and then combined with 100 μL of the cell suspension obtained as described above to initiate the reaction. After incubating at 30° C. for 1 hour, an aliquot of the reaction mixture was combined with a doubled volume of methanol, stirred thoroughly, centrifuged to remove the cell and recover a supernatant which was then subjected to a gas chromatography. Disappearance rate of the amino compound was compared as a relative value based on the value 100 at pH 6 (citrate buffer).

TABLE 3

| Reaction pH | Type of buffer | 1-Phenylethylamine disappearance rate (%, relative value) |
| --- | --- | --- |
| 5 | Sodium citrate | 63 |
| 6 | Sodium citrate | 100 |
| 6 | Potassium phosphate | 96 |
| 7 | Potassium phosphate | 84 |
| 8 | Potassium phosphate | 56 |
| 8 | Tris-HCl | 61 |
| 9 | Tris-HCl | 33 |
| 9 | Glycine | 34 |
| 10 | Glycine | 31 |
| 11 | Sodium carbonate | 25 |

Example 7

630 μL of an aqueous solution of 1-phenylethylamine as a racemic mixture obtained by dissolving 200 μL of 1-phenylethylamine as a racemic mixture and 900 μL of a 2N aqueous solution of sulfuric acid in 100 ml of distilled water was combined with 100 μL of a 2.2% (w/v) aqueous solution of sodium pyruvate and further combined with 100 μL of glycine buffer at pH 9 and 70 μL of distilled water, and then combined with 100 μL of a cell suspension obtained similarly as in Section (1) of Example 6 to initiate the reaction. After incubating at each temperature ranging from 20° C. to 60° C. for 1 hour, an aliquot of the reaction mixture was combined with a doubled volume of methanol. The mixture was stirred thoroughly, centrifuged to remove the cell and recover a supernatant which was then subjected to a quantification by a gas chromatography. Disappearance rate of the amino compound was compared as a relative value based on the value 100 at 50° C.

TABLE 4

| Reaction temperature (° C.) | 1-Phenylethylamine disappearance rate (%, relative value) |
| --- | --- |
| 20 | 14 |
| 30 | 22 |
| 40 | 40 |
| 50 | 100 |
| 60 | 89 |

Example 8

1370 μL of a 0.02% (w/v) aqueous solution (pH 9.0) of 1-(2,4-dichlorophenylethylamine as a racemic mixture was combined with 200 μL of a 2.2% (w/v) aqueous solution of sodium pyruvate and 230 μL of 100 mM glycine buffer (pH 9.0) and then combined with 200 μL of the cell suspension obtained in Section (1) of Example (6), and incubated at 30° C. for 110 hours. An aliquot of the reaction mixture was combined with a doubled volume of methanol and stirred thoroughly and centrifuged to remove the cell and recover a supernatant which was then subjected to a quantification by a gas chromatography. The results indicated that 46% of 1-(2,4-dichlorophenyl)ethylamine was lost. The remaining reaction mixture was adjusted at pH 12 with an aqueous solution of sodium hydroxide and then the residual 1-(2,4-dichlorophenyl)ethylamine was extracted into diethylether. The optical purity of 1-(2,4-dichlorophenyl)ethylamine in the extract was determined by HPLC and the results indicated that the ratio of (R)-form/(S)-form was 20/80.

Example 9

2 mL of the enzyme solution obtained in Example 1 was subjected 4 times to HPLC on a reverse phase column. The reverse phase column HPLC was performed in a condition described below.

[Reverse Phase HPLC Condition]
- Column: Protein-RP, 250 mm×4.6 mmID, particle size: 5 μm (YMC (KK))
- Column temperature: Room temperature
- Flow rate: 1 ml/min
- Detection: UV 230 nm
- Eluent A: Distilled water containing 0.1% trifluoroacetic acid
- Eluent B: Acetonitrile containing 0.08% trifluoroacetic acid
- Eluting condition: A sample was applied onto a column equilibrated with Eluent A and then the ratio of Eluent B was increased from 0% to 80% over a period of 40 minutes, whereby effecting an elution with a solvent mixture of Eluent A and Eluent B.

A fraction eluted at a ratio of Eluent B around 60% was obtained. The obtained fraction (3 mL aliquot) was lyophilized, and a part of the lyophilized sample was subjected to a gas phase protein sequencer 470 A (APPLIED BIOSYSTEMS) to determine an amino acid sequence of an amino terminal of the protein of the present invention. The results indicated that the protein of the present invention has an amino acid sequence represented by Sequence ID No. 3.

The remainder of the lyophilized sample was dissolved in distilled water and combined with 2 μl of a 1 mg/ml trypsin solution, and kept at 37° C. for 24 hours. After this period, the solution was subjected to a reverse phase HPLC to isolate and purify trypsin-digested fragments. The condition of the reverse phase HPLC was as described below.

[Reverse Phase HPLC Conditions]

Column: ODS-A211, 250 mm×4.6 mmID, particle size: 5 μm (SUMIKA CHEMICAL ANALYSIS SERVICE, LTD)

Column temperature: Room temperature

Flow rate: 1 ml/min

Detection: UV 230 nm

Eluent A: 0.1% Trifluoroacetic acid/water

Eluent B: 0.08% Trifluoroacetic acid/acetonitrile

Eluting condition: A sample was applied onto a column equilibrated with a solvent mixture of 95% Eluent A:5% Eluent B and the ratio of Eluent B was increased to 65% over a period of 60 minutes, whereby effecting an elution with a solvent mixture of Eluent A and Eluent B.

Each trypsin-digested fragment obtained was examined for its amino acid sequence similarly as described above. The results indicated that the digested fragment had the amino acid sequences represented by Sequence ID Nos.4 and 5.

Example 10
(Acquisition of DNA having a Partial Nucleotide Sequence of Inventive Gene)

(1) Preparation of Chromosome DNA of *Mycobacterium Aurum* Strain SC-S423

A sterilized medium containing 0.5% (w/v) glucose, 1.0% (w/v) peptone, 1.25% (w/v) yeast extract, 1.0% (w/v) malt extract and 0.5% (w/v) sodium chloride was inoculated with *Mycobacterium aurum* strain SC-S423 and cultivated for 64 hours and then 1000 mL of the culture obtained was centrifuged to harvest cells. The cells thus obtained was re-suspended in 900 ml of a sterilized medium containing 100 μg/ml D-cycloserine, 1.4% (w/v) glycine, 60 mM EDTA and 200 μg/ml lysozyme and incubated at 30° C. for 21 hours.

900 mL of this resultant suspension was centrifuged to harvest cells. The cell thus obtained was re-suspended in 10 ml of a buffer solution (pH 8.0, 50 mM Tris, 50 mM EDTA, 100 mM sodium chloride). To the suspension, SDS was added at a final concentration of 0.5%, and Proteinase K (Boehringer Mannheim) was further added at a final concentration of 200 μg/ml, and the mixture was incubated at 55° C. for 18 hours.

From the suspension after incubation, DNA was extracted by a phenol:chloroform:isoamylalcohol method, and the extracted fraction was combined with ethanol which had been kept at −20° C. and DNA precipitating out was wound onto a glass rod. This DNA was air-dried, dissolved in a TE buffer solution (10 mM Tris, 1 mM EDTA, pH 8.0), which was combined with an RNAase at a final concentration of 50 μg/ml, and kept at 37° C. for 1 hour. This was employed as a chromosome DNA sample.

(2) Primer Synthesis

Based on an amino acid sequence represented by Sequence ID No. 4, a mixture (hereinafter referred to as Primer G-24-1) of the oligonucleotide having an nucleotide sequence represented by Sequence ID No. 6 was synthesized. Also based on an amino acid sequence represented by Sequence ID No. 5, a mixture (hereinafter referred to as Primer RG32-1) of the oligonucleotide having a nucleotide sequence represented by Sequence ID No. 7 was synthesized. The synthesis of an oligonucleotide was performed using an automatic DNA synthesizer Model 380 A (APPLIED BIOSYSTEMS).

(3) PCR Amplification and Cloning of DNA having a Partial Nucleotide Sequence of the Gene of the Presnet Invention [I]

Using Primer G24-1 and Primer RG32-1 synthesized in Section (2) of Example 10, PCR was performed employing as a template the chromosome DNA prepared in Section (1) of Example 10. The PCR was performed in a condition described below. The reaction mixture was prepared using an Advantage cDNA PCR Kit available from CLONTECH.

[Reaction Mixture Composition]

Chromosome DNA sample (1 ng/μl) 1 μl

Primers (each 10 pM) Each 0.5 μl×2 types

×50 dNTPs mix (each 10 mM) 0.5 μl

×10 cDNA PCR Reaction Buffer 2.5 μl

×50 Advantage cDNA Polymerase Mix 0.5 μl

Sterile redistilled water 19.5 μl

[Temperature Conditions]

1) 94° C. 1 minute 2) 94° C. 30 seconds 3) 68° C. 3 minutes 4) 94° C. 20 seconds 5) 68° C. 3 minutes 6) 68° C. 3 minutes A cycle consisting of steps 4) and 5) was repeated 34 times.

After the reaction, the reaction mixture was subjected to an agarose gel electrophoresis and the products were examined, and the results revealed that about 800 bp DNA was amplified. This DNA was ligated into a "PCR Product insertion site" of plasmid vector pCRII using a TA cloning kit (Invitrogen), and the ligated DNA was transduced into *E. coli* strain JM109 (using compitent high JM109 from TOYOBO Co., Ltd.) to obtain transformants.

Subsequently, a plasmid DNA possessed by the transformant obtained was prepared and sequenced using a Dye Terminator Cycle Sequencing Ready Reaction kit and an automatic nucleotide sequencer Model 373 A. The results revealed that this plasmid contained a DNA having a nucleotide sequence (730 bp) of nucleotide's positions Nos.231 to 960 in the nucleotide sequence represented by Sequence ID No. 2.

(4) PCR Amplification and Cloning of DNA having Partial Nucleotide Sequence of the Gene of the Present Invention [II]

Based on the nucleotide sequence of 730 bp obtained in Section (3) of Example 10, an oligonucleotide having a nucleotide sequence represented by Sequence ID No. 8 was synthesized.

A chromosome DNA prepared by the method described in Section (1) of Example 10 was cleaved partially with a restriction enzyme Sau3A1 and ligated with a multi-cloning site of plasmid vector pUC118. Then PCR was performed using as a template the ligated DNA and as primers an oligonucleotide having the nucleotide sequence represented by Sequence ID No. 8 and RV primer (TAKARA SHUZO Co., Ltd.). The PCR was performed in a condition described below. The reaction mixture was prepared using an Advantage cDNA PCR Kit available from CLONTECH.
[Reaction Mixture Composition]
Template DNA 5 μl
Primer (each 10 μM) Each 1 μl×2 types
×50 dNTP mix (each 10 mM) 1 μl
×10 cDNA PCR Reaction Buffer 5 μl
×50 Advantage cDNA polymerase Mix 1 μl
Sterile redistilled water 36 μl
[Temperature Conditions]
1) 94° C. (1 minute)
2) 94° C. (0.5 minute)
3) 68° C. (3 minutes)
4) 68° C. (3 minutes)

A cycle consisting of steps 2) and 3) was repeated 30 times.

After the reaction, the reaction mixture was subjected to an agarose gel electrophoresis and the products were examined, and the results revealed that about 1 kbp DNA was amplified. This DNA was ligated into "PCR Product insertion site" of plasmid vector pCRII using a TA cloning kit (Invitrogen), and the ligated DNA was transduced into *E. coli* strain JM109 (using compitent high JM109 from TOYOBO Co., Ltd.) to obtain transformants.

Subsequently, a plasmid DNA possessed by the transformant obtained was prepared and sequenced similarly as in Section (3) of Example 10. The results revealed that this plasmid contained a nucleotide sequence of nucleotide's positions Nos.1 to 230 in the nucleotide sequence represented by Sequence ID No. 2.

(5) PCR Amplification and Cloning of DNA having a Partial Nucleotide Sequence of the Gene of the Present Invention [III]

Based on the nucleotide sequence of 730 bp obtained in Section (3) of Example 10, an oligonucleotide having a nucleotide sequence represented by Sequence ID No. 9 and an oligonucleotide having a nucleotide sequence represented by Sequence ID No. 10 were synthesized.

A chromosome DNA prepared by the method described in Section (1) of Example 10 was cleaved with a restriction enzyme EcoRI and ligated with an EcoRI Cassette (TAKARA SHUZO Co., Ltd). The reaction mixture was prepared using a Takara LA PCR in vitro Cloning Kit available from TaKaRa. The condition employed was as follows.
[Reaction Mixture Composition]
Restriction enzyme-treated DNA 5 μl
EcoRI Cassette 2.5 μl (20 ng/μl)
Ligation kit ver2 soln I 15 μl
Ligation kit ver2 soln II 7.5 μl After reacting at 16° C. for 30 minutes, the DNA was recovered by an ethanol precipitation and dissolved in 5 μl of TE buffer.

1 μl of the solution of DNA thus obtained was admixed with 13.5 μl of sterile redistilled water and heated at 94° C. for 10 minutes. Using this as a template and the oligonucleotide having the nucleotide sequence represented by Sequence ID No. 9 and a Cassette Primer C1 (TaKaRa) as primers, PCR was performed. The PCR was performed in a condition described below. The reaction mixture was prepared using a Takara LA PCR in vitro Cloning Kit available from TaKaRa.
[Reaction Mixture Composition]
Template DNA 14.5 μl
Primers (each 10 μM) Each 1 μl×2 types
dNTPs 8 μl
×2 GC Buffer 25 μl
LA Taq 0.5 μl (2.5 U)
[Temperature Conditions]
1) 94° C. (0.5 minute)
2) 55° C. (2 minutes)
3) 72° C. (3 minutes)

A cycle consisting of steps 1) to 3) was repeated 30 times.

Subsequently, the mixture after the reaction described above was subjected to a 10-fold dilution and a 1 μl aliquot was used as a template and an oligonucleotide having the nucleotide sequence represented by Sequence ID No. 10 and a Cassette Primer $C_2$ (TaKaRa) were used as primers to perform PCR. The PCR was performed in a condition described below. The reaction mixture was prepared using a Takara LA PCR in vitro Cloning Kit available from TaKaRa.
[Reaction Mixture Composition]
Template DNA 1 μl
Primers (each 10 μM) Each 1 μl×2 types
dNTPs 8 μl
×2 GC Buffer 25 μl
LA Taq 0.5 μl (2.5 U)
Sterile redistilled water 13.5 μl
[Temperature Conditions]
1) 94° C. (0.5 minute)
2) 55° C. (2 minutes)
3) 72° C. (3 minutes)

A cycle consisting of steps 1) to 3) was repeated 30 times.

After the reaction, the reaction mixture was subjected to an agarose gel electrophoresis and the products were examined, and the results revealed that about the DNA was amplified. This DNA fragment was recovered from the gel, and cloned into a pT7blue T-vector (Novagen). The DNA of a resultant plasmid was prepared and subjected to nucleotide sequencing similarly as in Section (3) of Example 10. As a result, this plasmid was revealed to contain a nucleotide sequence of nucleotide's positions Nos. 961 to 1020 of the nucleotide sequence represented by Sequence ID No. 2. (part of the side of C-terminal)

The result of Examples 10 (3) to (5) revealed that a gene derived from *Mycobacterium aurum* SC-S423 contains a nucleotide sequence represented by Sequence ID No.2.

Example 11

(Acquisition of a Modified Gene DNA)

Based on the nucleotide sequence represented by Sequence ID No. 2 obtained in Sections (3) to (5) of Example 10, an oligonucleotide having a nucleotide sequence represented by Sequence ID No. 11 (hereinafter referred to as Primer F-4/NcoI) and an oligonucleotide having a nucleotide sequence represented by Sequence ID No. 12 (hereinafter referred to as Primer R1030/BamHI) were synthesized.

Using Primer F-4/NcoI and Primer R1030/BamHI together with the chromosome DNA prepared by the method described in Section (1) of Example 10 as a template, PCR was performed. The PCR was performed in a condition described below. The reaction mixture was prepared using Expand High Fidelity PCR System available from Boehringer Mannheim.
[Reaction Mixture Composition]
Genome DNA stock solution (0.1 μg/μl) 1 μl
Primers (each 4 pmol/μl) Each 5 μl×2 types
dNTPs mix (each 2.5 mM) 8 μl
×10 Expand HF buffer with 15 mM $MgCl_2$ 10 μl
Expand High Fidelity PCR System enzyme mix 0.75 μl Sterile redistilled water 71 μl
[Temperature Conditions]
1) 95° C. (2 minutes)
2) 96° C. (15 seconds)
3) 60° C. (15 seconds)
4) 72° C. (1 minute)
5) 72° C. (10 minutes)

A cycle consisting of steps 2) to 4) was repeated 25 times.

The PCR fragments were cleaved with NcoI and BamHI and purified using a Qiagen purple spin column (Quiagen). The purified DNA was ligated to the NcoI and BamHI sites downstream of trc promoter in plasmid vector pTrc99a (Amersham Pharmacia Biotech), and the ligated DNA was transduced into E. coli strain JM109 to obtain transformants. The plasmid possessed by the transformant thus obtained was designated as ptrc9. Subsequently, nucleotide sequence of this plasmid ptrc9 was determined as described above using an ABI Prism sequencing kit (Perkin Elmer). The results revealed that the ptrc9 contained a modified gene DNA as the gene of the present invention whose nucleotide sequence comprising a nucleotide substitution from adenine to guanine occurring at a position corresponding to nucleotide's position No.4 of a nucleotide sequence (1020 bp) of nucleotide's positons Nos. 1 to 1020 in the nucleotide sequence represented by Sequence ID No. 2. Such this manner can be easily used as a transduction method of nucleotide substitution, and whereby the modified gene DNA as the gene of the present invention can be obtained.

Example 12

A 50 ml sterilized LB medium containing ampicillin (50 μg/ml) and IPTG (1 mM) was inoculated with the transformant E. coli strain JM109/ptrc9 prepared in Example 11 and cultivated with shaking overnight at 30° C. and then cells were harvested by centrifugation and suspended in 470 μl of 100 mM potassium phosphate buffer (pH 6.0).

The cell suspension described above was combined with 530 μl of 100 mM potassium phosphate buffer (pH 6) containing 10 μmoles of acetophenone, 400 μmoles of a racemic mixture of sec-butylamine and 0.02 μmoles of pyridox-5-phosphate (PLP), and the mixture was kept at 40° C. for 6 hours at 130 rpm. After this period, the reaction mixture was subjected to quantitative analysis of 1-phenylethylamine. As a result, 0.45 mM 1-phenylethylamine was detected in the reaction mixture, with the optical isomer ratio of the R-form being 100%.

Example 13

A 5 ml sterilized LB medium containing ampicillin (50 μg/ml) and IPTG (1 mM) was inoculated with the transformant E. coli strain JM109/ptrc9 prepared in Example 11 and cultivated with shaking overnight at 30° C. and then cells were harvested by centrifugation and suspended in 280 μl of 100 mM potassium phosphate buffer (pH 6.0).

The cell suspension thus obtained was combined with 720 μl of 100 mM potassium phosphate buffer (pH 6) containing 10 μmoles of a racemic mixture of 1-phenylethylamine, 20 μmoles of sodium pyruvate and 0.02 μmoles of pyridoxal-5-phosphate (PLP), and the mixture was kept at 40° C. for 6 hours at 130 rpm. After this period, the reaction mixture was subjected to quantitative analysis of 1-phenylethylamine. As a result, a 50% recovery of 1-phenylethylamine was observed, with the optical purity of the S-form being 99.5 e.e.%.

Example 14

280 μl of the cell suspension prepared by the method similar to that in Example 13 was combined with 720 μl of 100 mM potassium phosphate buffer (pH 6) containing 10 μmoles of (R)-1-phenylethylamine, 20 μmoles of sodium pyruvate and 0.02 μmoles of pyridoxal-5-phosphate (PLP), and the mixture was kept at 40° C. for 7 minutes at 130 rpm. After this period, the reaction mixture was subjected to quantitative analysis of an optically active amino acid, and the results indicated the formation of 5.9 mM alanine, with an optical purity of the D-form being 73.8% e.e.

Example 15

A 30 ml sterilized LB medium containing ampicillin (50 μg/ml) and IPTG (1 mM) was inoculated with the transformant E. coli strain JM109/ptrc9 prepared in Example 11 and cultivated with shaking overnight at 30° C. and then cells were harvested by centrifugation and suspended in 200 μl of 100 mM potassium phosphate buffer (pH 6.0).

The cell suspension described above was combined with 820 μl of 100 mM phosphate buffer (pH 6) containing 30 μmoles of (R)-1-phenylethylamine, 30 μmoles of lithium β-hydroxypyruvate and 0.02 μmoles of pyridoxal-5-phosphate (PLP), and the mixture was kept at 40° C. for 60 minutes with shaking at 130 rpm. After this period, the reaction mixture was subjected to quantitative analysis of an optically active amino compound, and the results indicated the formation of 24.5 mM serine, with an optical purity of the D-form being 99.4 e.e.%.

What is claimed is:

1. An isolated protein comprising an amino acid sequence represented by SEQ ID NO. 1, wherein said protein converts acetophenone to an optically active 1-phenylethylamine in the presence of a racemic mixture of sec-butylamine.

2. An isolated protein comprising an amino acid sequence represented by SEQ ID NO. 1, wherein said protein converts acetophenone to an optically active 1-phenylethylamine in the presence of a racemic mixture of sec-butylamine, and wherein said protein has a single amino acid substitution within Sequence ID No. 1.

3. The isolated protein of claim 2, wherein alanine is substituted for threonine at position number 2 in SEQ ID NO. 1.

4. An isolated protein comprising an amino acid sequence which has at least 60% sequence identity to SEQ ID NO. 1, wherein said protein converts acetophenone to an optically active 1-phenylethylamine in the presence of a racemic mixture of sec-butylamine and wherein said protein has a molecular weight of about 37 kDa as a monomer, and is obtainable from *Mycobacterium aurum* SC-S432.

5. An isolated protein comprising an amino acid sequence which has at least 90% sequence identity to SEQ ID NO. 1, wherein said protein converts acetophenone to an optically active 1-phenylethylamine in the presence of a racemic mixture of sec-butylamine.

6. The isolated protein of claim 5, wherein said protein has at least 95% sequence identity to SEQ ID NO. 1.

7. An isolated protein comprising an amino acid sequence which has at least 80% sequence identity to SEQ ID NO. 1, wherein said protein converts acetophenone to an optically active 1-phenylethylamine in the presence of a racemic mixture of sec-butylamine, and wherein said protein has a molecular weight of about 37 kDa as a monomer.

8. The isolated protein of claim 7, wherein said protein has at least 90% sequence identity to SEQ ID NO. 1.

9. The isolated protein of claim 8, wherein said protein has at least 95% sequence identity to SEQ ID NO. 1.

10. An isolated protein comprising an amino acid sequence which has at least 80% sequence identity to SEQ ID NO. 1, wherein said protein converts acetophenone to an optically active 1-phenylethylamine in the presence of a racemic mixture of sec-butylamine, and wherein said protein is derived from a microorganism belonging to the genus Mycobacterium.

11. The isolated protein of claim 10, wherein said protein has at least 90% sequence identity to SEQ ID NO. 1.

12. The isolated protein of claim 11, wherein said protein has at least 95% sequence identity to SEQ ID NO. 1.

13. An isolated protein comprising an amino acid sequence represented by amino acids 23 to 339 of SEQ ID NO. 1, wherein said protein converts acetophenone to an optically active 1-phenylethylamine in the presence of a racemic mixture of sec-butylamine.

* * * * *

SEQUENCE LISTING

<160> NUMBER OF SEQ ID NOS: 12

<210> SEQ ID NO 1
<211> LENGTH: 339
<212> TYPE: PRT
<213> ORGANISM: Mycobacterium aurum
<220> FEATURE:
<223> OTHER INFORMATION: SC-S423

<400> SEQUENCE: 1

Met Thr Ala Leu Ser Asp Leu Gly Thr Ser Asn Leu Val Ala Val Glu
 1               5                  10                  15

Pro Gly Ala Ile Arg Glu Asp Thr Pro Ala Gly Ser Val Ile Gln Tyr

```
                    20                  25                  30
Ser Asp Tyr Glu Leu Asp Thr Ser Ser Pro Phe Ala Gly Gly Val Ala
                35                  40                  45

Trp Ile Glu Gly Glu Tyr Leu Pro Ala Glu Ala Lys Ile Ser Ile
    50                  55                  60

Phe Asp Thr Gly Phe Gly His Ser Asp Leu Thr Tyr Thr Val Ala His
65                  70                  75                  80

Val Trp His Gly Asn Ile Phe Arg Leu Gly Asp His Leu Asp Arg Leu
                85                  90                  95

Leu Asp Gly Ala Ser Lys Leu Arg Leu Asp Ala Gly Tyr Ser Lys Asp
                100                 105                 110

Glu Leu Ala Glu Ile Thr Lys Lys Cys Val Ser Met Ser Gln Leu Arg
                115                 120                 125

Glu Ser Phe Val Asn Leu Thr Val Thr Arg Gly Tyr Gly Lys Arg Lys
            130                 135                 140

Gly Glu Lys Asp Leu Ser Lys Leu Thr His Gln Val Tyr Ile Tyr Ala
145                 150                 155                 160

Ile Pro Tyr Leu Trp Ala Phe Pro Pro Ala Glu Gln Ile Phe Gly Thr
                165                 170                 175

Thr Ala Ile Val Pro Arg His Val Arg Arg Ala Gly Arg Asn Thr Val
                180                 185                 190

Asp Pro Thr Ile Lys Asn Tyr Gln Trp Gly Asp Leu Thr Ala Ala Ser
                195                 200                 205

Phe Glu Ala Lys Asp Arg Gly Ala Arg Thr Ala Ile Leu Leu Asp Ser
210                 215                 220

Asp Asn Cys Val Ala Glu Gly Pro Gly Phe Asn Val Cys Ile Val Lys
225                 230                 235                 240

Asp Gly Lys Leu Ala Ser Pro Ser Arg Asn Ala Leu Pro Gly Ile Thr
                245                 250                 255

Arg Lys Thr Val Phe Glu Leu Ala Asp Gln Met Gly Ile Glu Ala Thr
                260                 265                 270

Leu Arg Asp Val Thr Ser Arg Glu Leu Tyr Asp Ala Asp Glu Leu Met
                275                 280                 285

Ala Val Thr Thr Ala Gly Gly Val Thr Pro Ile Asn Ser Leu Asp Gly
                290                 295                 300

Glu Ala Val Gly Asn Gly Glu Pro Gly Pro Leu Thr Val Ala Ile Arg
305                 310                 315                 320

Asp Arg Phe Trp Ala Leu Met Asp Glu Pro Gly Pro Leu Ile Glu Thr
                325                 330                 335

Ile Glu Tyr

<210> SEQ ID NO 2
<211> LENGTH: 1020
<212> TYPE: DNA
<213> ORGANISM: Mycobacterium aurum
<220> FEATURE:
<223> OTHER INFORMATION: SC-S423
<221> NAME/KEY: CDS
<222> LOCATION: (1)..(1017)

<400> SEQUENCE: 2 atg act gct ctt tca gac ctc ggc acc tcc aac ctg gtg gcc gtc gag     48
Met Thr Ala Leu Ser Asp Leu Gly Thr Ser Asn Leu Val Ala Val Glu
1               5                   10                  15 ccc ggc gcc atc cgc gag gac acc ccg gcc ggc tcg gtg atc cag tac     96
Pro Gly Ala Ile Arg Glu Asp Thr Pro Ala Gly Ser Val Ile Gln Tyr
```

```
                    20                     25                       30
agc gac tac gaa ctg gac acc tcc agc ccg ttc gcc ggc ggc gtc gcc        144
Ser Asp Tyr Glu Leu Asp Thr Ser Ser Pro Phe Ala Gly Gly Val Ala
         35                      40                      45 tgg atc gag ggc gaa tac ctg ccg gcc gaa gaa gcg aag atc tcc atc        192
Trp Ile Glu Gly Glu Tyr Leu Pro Ala Glu Glu Ala Lys Ile Ser Ile
     50                      55                      60 ttc gac acc gga ttc ggt cat tcc gat ctg acc tac acc gtc gcg cat        240
Phe Asp Thr Gly Phe Gly His Ser Asp Leu Thr Tyr Thr Val Ala His
 65                      70                      75                  80 gta tgg cac ggc aac atc ttc cgg ctc ggc gac cac ctg gac cgg ttg        288
Val Trp His Gly Asn Ile Phe Arg Leu Gly Asp His Leu Asp Arg Leu
                     85                      90                      95 ctc gac ggg gcg tcc aag ctg cgc ctg gac gcc ggg tac agc aag gac        336
Leu Asp Gly Ala Ser Lys Leu Arg Leu Asp Ala Gly Tyr Ser Lys Asp
                100                     105                     110 gaa ctg gcc gag atc acc aag aag tgc gtg tcg atg tcg cag ctg cgc        384
Glu Leu Ala Glu Ile Thr Lys Lys Cys Val Ser Met Ser Gln Leu Arg
            115                     120                     125 gaa tcg ttc gtg aat ctg acc gtc acc cgg gga tac gga aag cgc aag        432
Glu Ser Phe Val Asn Leu Thr Val Thr Arg Gly Tyr Gly Lys Arg Lys
        130                     135                     140 ggc gag aag gac ctg tcc aag ctc acc cat cag gtg tac atc tac gcc        480
Gly Glu Lys Asp Leu Ser Lys Leu Thr His Gln Val Tyr Ile Tyr Ala
145                     150                     155                 160 atc ccg tac ctg tgg gcc ttc ccg ccc gcc gag cag atc ttc ggc acc        528
Ile Pro Tyr Leu Trp Ala Phe Pro Pro Ala Glu Gln Ile Phe Gly Thr
                165                     170                     175 acc gcg atc gtg ccg cgc cat gtc cgc cgc gcc ggc cgc aac acc gtc        576
Thr Ala Ile Val Pro Arg His Val Arg Arg Ala Gly Arg Asn Thr Val
            180                     185                     190 gac ccg acc atc aag aac tac cag tgg ggt gat ctc acc gca gcc agt        624
Asp Pro Thr Ile Lys Asn Tyr Gln Trp Gly Asp Leu Thr Ala Ala Ser
        195                     200                     205 ttc gaa gcc aag gac cgt ggt gcg cgc acc gcg atc ctg ctc gac tcg        672
Phe Glu Ala Lys Asp Arg Gly Ala Arg Thr Ala Ile Leu Leu Asp Ser
    210                     215                     220 gac aac tgc gtg gcc gaa ggt ccg ggc ttc aac gtg tgc atc gtc aag        720
Asp Asn Cys Val Ala Glu Gly Pro Gly Phe Asn Val Cys Ile Val Lys
225                     230                     235                 240 gac ggc aag ctg gcc tcc ccg tcc cgg aac gcg ttg ccg ggc atc acc        768
Asp Gly Lys Leu Ala Ser Pro Ser Arg Asn Ala Leu Pro Gly Ile Thr
                245                     250                     255 cgt aag acg gtg ttc gaa ctg gcc gac cag atg ggc atc gaa gcc acc        816
Arg Lys Thr Val Phe Glu Leu Ala Asp Gln Met Gly Ile Glu Ala Thr
            260                     265                     270 ctg cgc gac gtc acc agc cgt gaa ctc tac gac gcc gac gag ttg atg        864
Leu Arg Asp Val Thr Ser Arg Glu Leu Tyr Asp Ala Asp Glu Leu Met
        275                     280                     285 gcg gtc acc acc gcg ggc ggg gtc aca ccg atc aac tcg ctg gat ggc        912
Ala Val Thr Thr Ala Gly Gly Val Thr Pro Ile Asn Ser Leu Asp Gly
    290                     295                     300 gag gcc gtg ggc aac ggc gag ccc ggt cca ctg acg gtg gcc atc cgg        960
Glu Ala Val Gly Asn Gly Glu Pro Gly Pro Leu Thr Val Ala Ile Arg
305                     310                     315                 320 gac cgg ttc tgg gcg ctg atg gac gag ccg ggc ccg ctg atc gaa acg       1008
Asp Arg Phe Trp Ala Leu Met Asp Glu Pro Gly Pro Leu Ile Glu Thr
                325                     330                     335 atc gaa tac tga                                                       1020
```

Ile Glu Tyr

<210> SEQ ID NO 3
<211> LENGTH: 18
<212> TYPE: PRT
<213> ORGANISM: Mycobacterium aurum
<220> FEATURE:
<223> OTHER INFORMATION: SC-S423
<221> NAME/KEY: UNSURE
<222> LOCATION: (4)
<221> NAME/KEY: UNSURE
<222> LOCATION: (9)

<400> SEQUENCE: 3

Thr Ala Leu Xaa Asp Leu Gly Thr Xaa Asn Leu Val Ala Val Glu Pro
1               5                   10                  15

Gly Ala

<210> SEQ ID NO 4
<211> LENGTH: 17
<212> TYPE: PRT
<213> ORGANISM: Mycobacterium aurum
<220> FEATURE:
<223> OTHER INFORMATION: SC-S423

<400> SEQUENCE: 4

Ile Ser Ile Phe Asp Thr Gly Phe Gly Ala Ser Asp Leu Thr Tyr Thr
1               5                   10                  15

Val

<210> SEQ ID NO 5
<211> LENGTH: 19
<212> TYPE: PRT
<213> ORGANISM: Mycobacterium aurum
<220> FEATURE:
<223> OTHER INFORMATION: SC-S423

<400> SEQUENCE: 5

Asp Arg Phe Trp His Leu Met Asp Glu Pro Gly Pro Leu Ile Glu Thr
1               5                   10                  15

Ile Glu Tyr

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (12)
<223> OTHER INFORMATION: i
<221> NAME/KEY: modified_base
<222> LOCATION: (18)
<223> OTHER INFORMATION: i

<400> SEQUENCE: 6
ttygayacsg gnttcggngc stcsgaycts acstayac                              38

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 7

-continued

```
ccsggctcgt ccatsagrtg ccagaascgr tc                                32

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 8
gagccggaag atgttgc                                                 17

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 9
ccaccctgcg cgacgtcacc agcc                                         24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
tctacgacgc cgacgagttg atgg                                         24

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 11
tgccatggct gctctttcag acctcggcac ct                                32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 12
gcggatccac tcagtattcg atcgtttcga tc                                32
```